(12) United States Patent
Honeycutt et al.

(10) Patent No.: US 8,517,909 B2
(45) Date of Patent: Aug. 27, 2013

(54) APPARATUS AND METHODS TO IMPROVE SLEEP, REDUCE PAIN AND PROMOTE NATURAL HEALING

(76) Inventors: James David Honeycutt, Washougal, WA (US); John C. Honeycutt, Dallas, TX (US)

( * ) Notice: Subject to any disclaimer, the term of this patent is extended or adjusted under 35 U.S.C. 154(b) by 0 days.

(21) Appl. No.: 13/292,333

(22) Filed: Nov. 9, 2011

(65) Prior Publication Data

US 2012/0053394 A1    Mar. 1, 2012

Related U.S. Application Data

(63) Continuation of application No. 11/307,348, filed on Feb. 1, 2006, now Pat. No. 8,088,057.

(60) Provisional application No. 60/593,647, filed on Feb. 1, 2005.

(51) Int. Cl.
*A61N 1/00* (2006.01)

(52) U.S. Cl.
USPC ............................................. 600/14; 600/27

(58) Field of Classification Search
USPC .................... 600/9–15, 26–28; 331/158–164
See application file for complete search history.

(56) References Cited

U.S. PATENT DOCUMENTS

| | | | |
|---|---|---|---|
| 3,946,745 A | 3/1976 | Hsiang-Lai et al. |
| 4,014,323 A | 3/1977 | Gilmer et al. |
| 4,428,366 A | 1/1984 | Findl et al. |
| 4,683,873 A | 8/1987 | Cadossi et al. |
| 4,765,310 A | 8/1988 | Deagle et al. |
| 4,915,110 A | 4/1990 | Kitov |
| 4,918,418 A | 4/1990 | Tsala |
| 5,138,172 A | 8/1992 | Krop |
| 5,156,587 A | 10/1992 | Montone |
| 5,216,326 A | 6/1993 | Lundgren |
| 5,441,495 A | 8/1995 | Liboff et al. |
| 5,450,859 A | 9/1995 | Litovitz |
| 5,453,073 A | 9/1995 | Markoll |
| 5,496,258 A | 3/1996 | Anninos et al. |
| 5,501,704 A | 3/1996 | Chang et al. |
| 5,634,939 A | 6/1997 | Kuster et al. |
| 5,752,911 A | 5/1998 | Canedo et al. |
| 6,108,580 A | 8/2000 | Greenspan et al. |
| 6,167,304 A | 12/2000 | Loos |
| 6,235,251 B1 | 5/2001 | Davidson |
| 6,290,638 B1 | 9/2001 | Canedo et al. |
| 6,485,963 B1 | 11/2002 | Goodwin et al. |
| 6,526,319 B2 | 2/2003 | Kobayashi |
| 6,560,490 B2 | 5/2003 | Grill et al. |
| 6,662,051 B1 | 12/2003 | Eraker et al. |
| 6,663,556 B2 | 12/2003 | Barker |
| 6,733,435 B2 | 5/2004 | Canedo |
| 6,760,627 B2 | 7/2004 | Carter et al. |
| 6,763,266 B1 | 7/2004 | Kroll |
| 6,794,407 B2 | 9/2004 | Lewy et al. |
| 6,845,270 B2 | 1/2005 | Debrouse |
| 6,955,642 B1 | 10/2005 | Simon |

*Primary Examiner* — Charles A Marmor, II
*Assistant Examiner* — Carrie R Dorna

(57) ABSTRACT

This is a new invention, which is safer, simpler to use, less invasive into a user's daily routine and provides a lower cost solution to existing pulsed magnetic field and related vibrational electromagnetic therapy devices to improve sleep, encourage natural healing and reduce pain. This is accomplished through Multiple Simultaneous Extremely Low Frequency (MSELF) energy waves. The MSELF energy waves are derived from a quartz crystal with a fundamental frequency less than one-half of one percent from a natural Fibonacci Number. The apparatus utilizes firmware operating in a microcontroller emulating Circadian Rhythms. The microcontroller is also clocked by the Fibonacci Number Quartz Crystal. Additionally, the apparatus's unique application of an H-Bridge configuration power-driver with Pulse Width Modulation (PWM) capabilities supports a novel approach to supply two simultaneous therapeutic frequencies.

19 Claims, 28 Drawing Sheets

Block Diagram of EnergyWave Therapy Device

Block Diagram of EnergyWave Therapy Device

Waveform Test Configuration

Tektronix 468 Oscilloscope
Sweep Speed 2ms/Division

Channel 1 - Ferrite Inductor Pick-up
50mV/Division - 180mV P/P

Channel 2 - Function Generator Out
Input Frequency 100 Hz Sine Wave
10V/Division - 15V P/P Gauss meter @ 8 inches above coil
measured 15 milliGauss Capture of Resultant Inductance and Magnetic Flux with
Sinusoidal Wave Driven Coil Capture of Resultant Inductance and Magnetic Flux with
Triangular Wave Driven Coil Tektronix 468 Oscilloscope
Sweep Speed 2ms/Division Channel 1 - Ferrite Inductor Pick-up
2V/Division - 7V P/P Channel 2 - Function Generator Out
Input Frequency 100 Hz Square Wave
10V/Division - 15 V P/P Gauss meter @ 8 inches above coil measured 100 milliGauss Capture of Resultant Inductance and Magnetic Flux with Square Wave Driven Coil

Figure 6

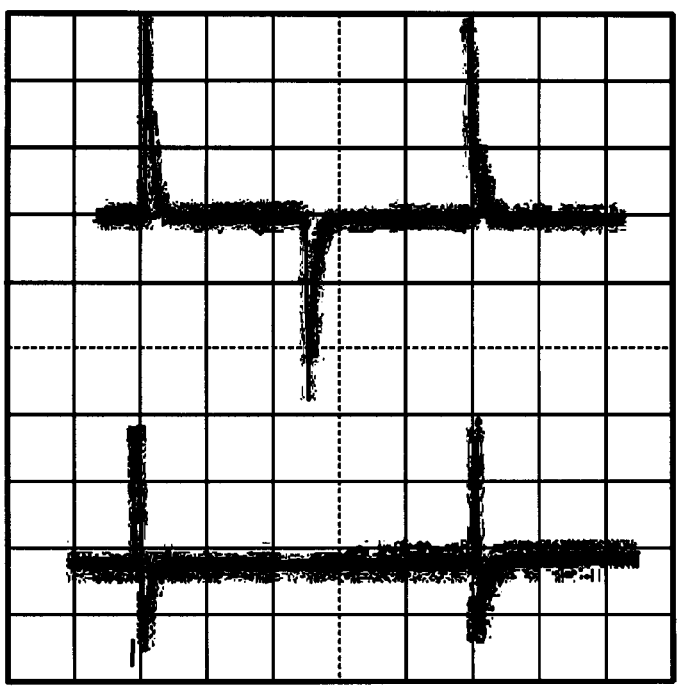

Tektronix 468 Oscilloscope
Sweep Speed 2ms/Division

Channel 1 - Ferrite Inductor Pick-up
Bipolar 24V Pulse @ 100Hz yields:
2V/Division - 12V P/P
Gauss meter @ 22 inches above coil measured 90 milliGauss Channel 2 - Ferrite Inductor Pick-up
Unipolar 12V Pulse @ 100Hz yields:
2V/Division - 6V P/P
Gauss meter @ 22 inches above coil measured 50 milliGauss Comparison of Resultant Inductance and Magnetic Flux between Bipolar and Unipolar Pulse Waveforms Demonstration of Multiple Simultaneous Extremely Low Frequency Waveforms Capability Using an H-Bridge with PWM and Direction Inputs Schematic of EnergyWave Therapy Device, Preferred Embodiment EnergyWave Therapy Device Assembly for Preferred Embodiment Figure 10 — Software Flowchart Program Tables and Memory Map Single LED User Interface Schematic Single LED User Interface Assembly Sleep Mat Flat Coil Spot Treatment Multiple Energy Attachment Spot Treatment Multiple Energy Assembly Water Foot-bath Multiple Energy Attachment Not Drawn to Scale Water Foot-Bath Multiple Energy Attachment Assembly Schematic for Alternative Lower Cost EnergyWave Therapy Device

Lower Cost Alternative Assembly

Requires External Power Wave Attachment, e.g. Sleep Mat Flat Coil

EnergyWave Therapy Typical Sleep
Application Method

EnergyWave Therapy Sleep Application Method
with External Flat Ribbon Cable Sleep Coil EnergyWave Therapy Waterless Foot-Bath Application Method EnergyWave Therapy Water Foot-Bath Application Method EnergyWave Therapy Local Application Method EnergyWave Therapy with Massage Application EnergyWave Therapy with Massage and Spot Treatment
Application Method Integrated EnergyWave Therapy Device - Alternative Embodiment

APPARATUS AND METHODS TO IMPROVE SLEEP, REDUCE PAIN AND PROMOTE NATURAL HEALING

CROSS-REFERENCE TO PARENT APPLICATION AND DISCLOSURE DOCUMENT

This non-provisional application is a continuation of U.S. patent application Ser. No. 11/307,348 filed Feb. 1, 2006 now U.S. Pat. No. 8,088,057, which claims the benefit of U.S. Provisional Application No. 60/593,647, filed Feb. 1, 2005 and U.S.P.T.O. Disclosure Document No. 561984, filed Oct. 1, 2004. The foregoing applications and disclosure document are herein incorporated by reference in their entireties.

STATEMENT REGARDING FEDERALLY SPONSORED RESEARCH OR DEVELOPMENT

No part of this invention is the result of any federally sponsored research or development. No government funds were used for any portion of this invention. Inventors claim and reserve all rights and privileges associated with this invention.

BACKGROUND OF THE INVENTION

1. Field of the Invention

This invention relates to the use of a Fibonacci number quartz crystal clocking a stored program microprocessor which controls an H-bridge in an exclusive-OR operation to mix two simultaneous and different therapeutic frequencies following circadian rhythms to generate unique electromagnetic pulses using various inductors and other emitters to improve sleep, reduce pain and increase natural healing.

2. Background Art

There exists a long history of using vibrational energies to affect an organism's wellbeing. These include a variety of vibrational energies from sound, light, heat, touch, and for more than the past two centuries, electromagnetic waves, since the discoveries of Voltaire, Faraday, Maxwell, Tesla and others. Some electromagnetic therapy devices create an ionizing field that attempts to destroy the parasitic organisms, pathogens or unhealthy cellular structures in an organism, sometimes to the detriment of healthy cells and organs. Others use the non-ionizing range of electromagnetic field (EMF) spectrum to restore the organism's natural frequencies to healthy ones through entrainment by superimposing strong wave energies for short periods of time with repeated applications. Some electromagnetic therapy devices use multiple types of energies (i.e. multiple ranges of the EMF spectrum). Some electromagnetic therapy devices use pure, sinusoidal wave frequencies; whereas others use saw-tooth, square wave, sharp spikes or other irregular waves in order to be rich in harmonics.

The uses of these alternative and complementary electromagnetic therapy devices have already been acknowledged by the current medical industry in the United States as beneficial in specific healing situations. Today there are thousands of electromagnetic therapy devices available for purchase. Even NASA has explored and reported on the benefits of this technology in nerve and tissue regeneration, the results of which resulted in granting U.S. Pat. No. 6,485,963.

When conventional cancer therapies failed to halt the spread of breast cancer, or even alleviate its symptoms in the wife of one of the inventors, the inventor started using several alternative electromagnetic therapy devices to help his wife. Two of the devices were successful in reducing some of the symptoms, but all the devices failed to halt the spread of the cancer and his wife eventually died from the cancer. The device which offered the most relief to his wife was a water foot-bath which reduced excessive swelling in her feet, ankles, and lower legs. Purportedly, the water foot-bath therapy device was drawing toxins and pathogens out of his wife's body through an energy transfer generated by an electrical field between parallel metal disks, or electrodes submerged in the water with his wife's feet.

While the water foot-bath therapy device was effective in reducing swelling it also turned the water brown to orange in color after a typical thirty minute treatment. Testing later revealed the discoloration was due to electroplating and oxidation effects of the metals used as the electrodes submersed in the water with the subject's feet. This required the washing of the subject's feet at the conclusion of the treatment to remove the metal byproducts on the subject's feet to prevent possible contamination. Additionally, the device sold for over $1,500 USD and required administration by a trained therapist or extensive personal training to be safely used.

While the inventor and his wife were away from home, without access to the water foot-bath therapy device, the inventor's wife began experiencing severe swelling in her feet and ankles. The inventor built a simple version of the water foot-bath using a 12 Volt DC, 2 Ampere power supply connected to two half-inch diameter copper pipes, six inches in length, located four-inches apart, each protected inside of multiple hole drilled one-inch diameter PVC pipes to prevent his wife's feet from coming in direct contact with the copper pipe electrodes, yet open enough to allow conduction through the water. Seawater was mixed with warm fresh water in a one to one ratio and placed in a three gallon tub approximately eighteen inches in diameter and ten inches high. The PVC protected copper tube electrodes were connected to the 12 VDC power supply. One copper pipe, referred to as the cathode, was connected to the negative output of the power supply, and the other copper pipe, referred to as the anode, was connected to the positive output of the power supply. The two electrodes were then placed in the water in the tub and the 12 VDC power supply was plugged into a 120 VAC power outlet. Voltage and current measurements were made with a digital multimeter to determine the levels within the water foot-bath were safe for submersing his wife's feet. The measurements confirmed the safety and the inventor's wife placed her feet into the energized water foot-bath. After a treatment time of 30 minutes the Power Supply was unplugged from the 120 VAC power outlet and the inventor's wife removed her feet from the water foot-bath. Her feet and ankles were noticeably less swollen after the first treatment and subsequent treatments further improved this condition. The inventor also noticed the water had a green color due to the oxidation of the copper. Additionally, the anode copper pipe was coated with a green residue (cuprous sulfate), and the cathode copper pipe was coated with a black residue. These residues had to be scraped off prior to the next use of the foot-bath.

The inventor recorded the usage of this and other electromagnetic therapy devices and methodologies employed to treat his wife. As a result of the positive results achieved with his simple water foot-bath device the inventor wanted to understand why some electromagnetic therapy devices were at least partially effective and others were not. The inventor partnered with another engineer/scientist with whom to collaborate in accomplishing these objectives.

Research, Testing and Observations

The inventors acquired a variety of currently available electromagnetic therapy devices to test the devices' effectiveness and ease of use. The tested electromagnetic therapy devices fell into one of four categories. First were high energy devices, which produce a large E (Voltage) field, some measuring over 45,000 volts, emitted through a gas in glass tube or other specialized antennae. Category one devices generated high energy frequencies which allegedly killed pathogens or parasites in the body. The second category included devices which produced an electrical stimulation in the body through low current emissions, usually through direct contact with the skin. Category two devices allegedly stimulated nerve cells to cause the body to attempt to initiate the healing process. The third category included devices which used LEDs, both in the visible and invisible infrared range of light, usually pulsing on and off at specific frequencies. Category three devices allegedly used both types of light waves to stimulate the subtle energy systems of the body to encourage natural healing. The fourth category included devices which used water as a medium to transfer vibrational energies to the test subject. Category four devices allegedly operated by setting up vibrations in the water causing the person's body to expel toxins through their feet submersed in the water. Devices from the second and fourth category had been successfully used with the first inventor's late wife to alleviate the symptoms resulting from the advancing cancer.

All of the electromagnetic therapy devices acquired and tested by the inventors had multiple disadvantages. First, the effective devices were relatively expensive, selling from $1,500 to over $10,000 USD. This was especially true when selling price was compared to the costs to produce a functionally equivalent unit. Applying accepted production to retail pricing formulae indicated an effective water foot-bath device should cost about $50 USD to build and retail for about $500 USD, not $1,500 USD.

Secondly, the effective units required a trained therapist to administer the treatment or extensive training for personal use. Even with training they often required another person to administer the therapy, following specific procedural steps or requiring the use of ancillary devices to be effective, to ensure they were safely administered, or to prevent damaging the device.

Thirdly, some electromagnetic therapy devices used subcutaneous electrodes to administer treatment. Other electromagnetic therapy devices administered uncomfortable electric shocks to the user. Category one devices required careful handling to avoid breaking the glass neon, or other gas, tube and to prevent potentially hazardous shocks to the user, as the voltage applied to the neon tube was 45,000 volts.

Finally, their use was invasive into the daily routine for both healthy and ill individuals. Typical therapy took an hour or longer for setup, administering the scheduled treatment, and subsequent clean-up.

None of the category three devices tested showed any level of effectiveness; yet these were the least expensive and simplest to use devices, but all to no avail.

As this research progressed the inventors determined to overcome the problems discovered both with their own foot-bath apparatus and with the other currently available devices. This was done towards developing low cost, effective, non-invasive and simple to use, self-administered electromagnetic therapy apparatuses to improve quality of life for their users. The inventors' research, development and testing resulted in discovering a number of non-obvious and novel methods to generate healthful waves of energy which reduce pain, improve sleep and promote natural healing. The claims and embodiments of the invention presented herein are the results of that effort.

Developing Energywave Therapy

After concluding the research and testing of existing devices and doing further research, the inventors determined to avoid using high energy category one devices, instead pursuing a homeopathic approach designed to stimulate the body's natural healing systems. They felt impressed to use vibrational energy waves to accomplish the desired outcomes. The inventors began with their own water foot-bath, determined to understand what made it effective and how it could be improved upon.

Blind tests were carried out to determine if simply placing the test subject's feet into a tub of seawater and freshwater mixed at the ratio of one-to-one would have the same effect. The results showed that there was no measurable improvement without the electrical current flowing at the same time. Significantly, it was discovered that something as simple as generating a small direct current through the water foot-bath could have such remarkable effects at such a low cost (less than $10 USD to build the afore described simple water foot-bath circuit). For simplicity, the use of mixing seawater with freshwater was replaced with using tap-water with a small amount of salt (one to two teaspoons per gallon) being added to ensure adequate conductivity between the electrodes.

Another observation was the use of copper for the electrodes caused a green discoloration in the water and on the test subject's feet. This prompted the testing of a variety of metals for their respective use as either or both anode (+) and cathode (−) submersed electrodes. Testing of possible electrode material included using copper, stainless steel, zinc, silver, gold and tungsten with the same 12 VDC, 2 Ampere power supply used above. In every case there was observable transference of metal oxides from the anode to the cathode, and in some instances to the test subject's feet. Additionally, the anode would become covered with its own oxide and rendered non-conductive, making the foot-bath ineffective after thirty to sixty minutes of use. This required the electrodes to be scraped clean after each treatment. After testing a variety of metals for use as electrodes it became obvious that the discoloration in the water was due to the electrolysis and electroplating effect between the electrodes, and not as a result of toxins being flushed from the body.

The first problem to be overcome was preventing any harmful metal byproducts from being released into the water that might contaminate the person receiving therapy. Continued research and further tests led the inventors to try carbon rods instead of metal for the electrodes. Common quarter-inch diameter non-plated carbon gouging rods used in arc welding were acquired and used as both the cathode and anode electrodes in the same water foot-bath. While there was still some depletion from the anode carbon rod, it did not discolor the water, nor negatively affect the subject. Carbon is also an inert element of which our bodies are composed. Six-inch long carbon rods were both effective and safe water foot-bath electrodes. Additionally, these common quarter-inch diameter gouging carbon rods used in arc welding are readily available at a very low cost, so this addressed one of the goals of keeping the product low in cost to produce.

The problem was the depletion of the positive anode material. While this was not as severe for the carbon rod anode, there was still carbon being depleted from the anode requiring its replacement at too frequent of an interval to be a commercially viable product. This problem prompted the idea of switching the current back and forth between the carbon rod electrodes to solve the anode material depletion problem. Further, it provided for the introduction of vibrational energies through the switching of the polarities, and hence the current, between the electrodes at a specific healing frequency. It was determined to use well-known Rife frequencies for this purpose.

The next challenge was how to reverse the polarities and hence the current flow between the electrodes in a simple, low cost manner. It was discovered that a low cost Integrated Circuit (IC) referred to as an H-Bridge, used to control power windows in automobiles, or for reversing the current flow through electric motors, and other inductive loads, could work in this method. A new water foot-bath device was then built and tested using the six-inch long, quarter-inch diameter carbon rods, a standard H-Bridge power driver and a 7.5 Hertz (Hz) CMOS divider circuit, derived from dividing down the standard US 60 Hz AC frequency, to drive the direction input of the H-Bridge. 7.5 Hz was chosen as it is a well-known Rife frequency and was easily derived from the 60 Hz AC line frequency. It was discovered switching the current flow using the direction input to the H-Bridge greatly increased the electrode life. After more than 100 hours of continuous use no appreciable depletion of the carbon rods was noted, and very little carbon was seen in the water. Additionally, the desired energy of the selected frequency (7.5 Hz) was transferred effectively to the user with normal tap water and a small amount of salt as noted above. No unusual discoloration of the water occurred and the healing benefits of the swelling reduction noticed previously continued. Further, by using an H-Bridge a 100 percent duty cycle was achieved, as current was flowing at all times, switching direction at the specified frequency.

The inventors decided the device should generate multiple frequencies to be able to treat multiple symptoms. The simple 60 Hz AC divider circuit was abandoned for a crystal controlled, CMOS based, multiple frequency generator circuit. A standard television Color Burst quartz crystal with a fundamental frequency of 3,579,545 Hz was used as the base frequency generator from which all the lower frequencies presented to the H-Bridge direction input were derived. Dividing down through a 14-stage binary divider and then through a programmable decade up/down counter allowed for the creation of 10 unique frequencies in the range of 5.5 Hz to 55 Hz for the direction input to the H-Bridge. As the H-Bridge supports both a direction input, which changes the direction of the current flowing between its output, and a Pulse Width Modulation (PWM) input, that varies the current flowing in either direction, the inventors discovered the PWM input could instead be used to mix a second higher frequency to the lower directional frequency. The 14-stage binary divider provided a second frequency tapped earlier in the division process was very close to 880 Hz, a broad spectrum Rife healing frequency. By applying the selected lower decade up/down counter frequencies to the Direction input of the H-Bridge and the higher 880 Hz frequency to the Pulse Width Modulation (PWM) input of the H-Bridge, two simultaneous frequencies were observed, creating a square wave output rich in harmonics. It was also observed that adding the 880 Hz to the water foot-bath application resulted in faster improvements. Extensive testing followed demonstrating the effectiveness of the new device to reduce a variety of symptoms, far beyond the scope of edemas and related swelling previously observed.

Infrared and visible red and amber LEDs were added to the foot-bath circuit. These were connected across the carbon rod electrodes in parallel strings with reverse polarity between the infrared and visible LEDs so that during one-half of the cycle the current flowing in one direction would power the infrared LEDs and in the other half of the cycle the reversed current would power the visible LEDs. Later this was updated to use two different wavelengths of infrared LEDs, 880 nm in one direction and 940 nm in the opposite, and the same for the two different wavelengths of visible LEDs, so that all times the user and water were being exposed to infrared and visible light of different wavelengths at the same frequency being used to drive the carbon rod electrodes. This can be seen in FIG. 17. This resulted in achieving a 100 percent duty cycle of light energies in addition to the 100 percent duty cycle of electrical energy transferred between the carbon rod electrodes and therefore to the subject being treated.

Another capability added to the new CMOS based crystal frequency controlled water foot-bath device was a sweep mode, where the device would run for two-and-a-half minutes and then increment to the next frequency for another two-and-a-half minutes and continue until all ten frequencies were run for the total twenty-five minute treatment time. It was noticed this sweep mode allowed a test subject to identify one or more frequencies that caused a noticeable physical response. For instance, one test subject had a history of intestinal parasites resulting from living in remote areas of Brazil for two years. After returning to the United States for more than two more years he continued to be plagued by the intestinal parasites with accompanying weight loss and diarrhea. Using the sweep program with the water foot-bath device, when the third frequency began (6.8 Hz), which is noted for treating parasites, he felt an uncomfortable sensation in his upper intestinal and abdominal region. The discomfort quit when the next frequency change occurred. The subject was unaware of the frequencies being used or of the effects to expect. The subject then began using the water foot-bath device every other day for a period of one month for 25 minutes at 6.8 Hz. Each time he reported a similar discomfort but also reported his diarrhea stopped and he was gaining weight for the first time in three years. After one month of treatment it appeared the parasites were gone and eighteen months later he was still symptom free.

In an attempt to understand why certain frequencies were more effective than others the inventors led them to the Fibonacci number sequence and they discovered the color burst crystal frequency was about one percent difference from a natural Fibonacci number. The Fibonacci sequence occurs throughout nature where the previous two numbers are added to create the next number in the sequence; such a sequence would be 1, 2, 3, 5, 8, 13, 21, 34, and so on. This number sequence can be seen in the arrangements of seed spirals in a sunflower, the number of petals in most flowers, and the spirals of a pine cone.

As the number sequence continues, the ratio between two adjacent values approaches the Divine Proportion known as Phi (pronounced fee) being the ratio of 1.618. This ratio also exists throughout nature. It can be seen in the increasing radii of the chambered nautilus and even in the proportions of the human body. These and other personal insights led to the understanding that the fundamental frequency from which all subsequent treatment frequencies would be derived must be based upon a natural Fibonacci number. This led to further testing of a variety of fundamental frequencies which is documented later.

Concurrent with the water foot-bath development and testing was a concern with reducing the suspected harmful impacts of EMF pollution resulting from the wide spread use of 60 Hz Alternating Current (AC) devices throughout our homes and work places. The inventors were investigating a method to superimpose an 880 Hz signal on household AC lines to reduce the harmful effects in household appliances reported by University of Washington researchers, when the inventors decided to try creating smaller field using low cost, widely available, 40 conductor flat ribbon cable, wrapped around a user's bed. By crimping the female connector normally to one end of the cable and then offsetting the male connector at the other end by one wire on one side and then tapping into the newly opened wire space in the male connector, the inventors were able to turn the 40 parallel wires into a 40 turn air-core coil. The H-Bridge water foot-bath circuit could easily drive such a coil and it was thus employed to test the flat ribbon coil for its effects upon human test subjects.

A 20 foot flat ribbon cable (with 40 turns, therefore a total wire length of 800 feet) was placed around the outside of the mattress of a queen sized bed and magnetic flux measurements were made. At 5.5 Hz the magnetic flux measured about 30 milliGauss over the entire top surface of the mattress. A shorter 16 foot ribbon cable was then made and folded at right angles to create a large rectangle three by five feet and was placed between the mattress and box springs, as it was difficult to keep the external ribbon cable coil in place around the outside of the mattress. Additional flux readings indicated similar magnetic fields were observed as before.

Testing began by one of the inventors sleeping on the bed thus equipped with the flat ribbon cable constructed coil, said coil having a DC resistance of approximately 40 ohms, with the crystal controlled CMOS based water foot-bath controller operating said coil continuously at 5.5 Hz (without the 880 Hz PWM active). The inventor reported he slept well and awakening feeling refreshed and energized. Additional coils were made as described above and the original water foot-bath test subjects began testing the new air-core flat ribbon sleep mat devices. One test subject who had insomnia reported she slept through the night for the first time in several years.

Testing continued through the summer of 2004 with both the water foot-bath with the carbon rod electrodes and the sleep-mat as the flat ribbon coil was referred to. Each person participating in the testing was required to sign a confidentiality agreement and a general release of liability, and to keep a journal of his or her experiences. At no time were any of the devices offered for sale. The overall test results showed test subjects slept better with than without the new sleep-mat device and generally reported having more energy upon awakening. Men and women who were plagued by frequent nighttime urinations reported having fewer urination episodes during the night. Several test subjects with restless leg syndrome reported significantly less muscle spasms and leg discomfort with much improved sleep. In general all the participants, whether using the water foot-bath or sleep mat, reported a more healthy feeling and reduced effects of stress. Thus the inventors had created a new apparatus which will be referred to herein as an Energy Wave Therapy Device to avoid confusion with existing electromagnetic therapy devices.

The test subjects generally preferred sleeping at 5.5 to 6.8 Hz and reported any higher frequencies induced vivid dreams. Women seemed to be more sensitive to the sleep-mat device, some reporting that if awakened during sleep by an outside influence they could 'feel' the vibrations. This was reported much less frequently by the male test subjects. This effect was reduced or eliminated by moving the sleep-mat to below the bed. It was noticed the sleep-mat should be a minimum of 8 inches and a maximum of 24 inches from the test subject to be most effective. This allowed the person to be in within the bipolar magnetic flux field measured to be of between ten to thirty milliGauss at 5.5 Hz.

Of particular interest was the sleep-mat test subjects reported similar health benefits as did the water foot-bath test subjects; yet the sleep-mat method was far less intrusive into the daily routines of the test subjects, increasing their tendency to use the device. This was one of the goals the inventors set, and their focus shifted to the sleep-mat application, reserving the use of the water foot-bath method for more severe complaints.

With this focus on the sleep-mat the inventors embarked on further lab testing to understand how the human body 'sees', or perceives, the pulses emitted by the sleep-mat's flat coil and to provide objective observations in addition to the subjective ones from the test subjects. The inventors embarked upon a series of tests as depicted in FIG. 2. These tests used both a Tektronix Model FG503 Signal Generator 22 and the previously described crystal controlled CMOS H-Bridge water foot-bath controller 28 identified as H-Bridge Test Signal generator, to drive a Flat Ribbon Cable Coil 25 through input 24 to the flat ribbon cable coil. A Ferrite Core Inductive Transducer 26 was constructed using approximately 215 feet of enamel covered #30 copper wire wound as a two-inch long coil on a three-and-a-half inch by three-eighths inch diameter ferrite rod. Ferrite Core Inductive Transducer 26 was terminated with a 10,000 ohm resistor to dampen the undesirable effects of high frequency ringing observed at about 27,000 Hz. It has been established that the human body has a +j or inductive reactance and Ferrite Core Inductive Transducer 26, when properly terminated, is an analog of the human body relative to observing the coupled energy wave as emitted into the body.

Ferrite Core Inductive Transducer 26 was placed directly on top of Flat Ribbon Cable Coil 25 to allow for adequate coupling between the two. A Tektronix Model 468 Storage Oscilloscope 21 was used to observe measure and record the effects of different waveforms. Oscilloscope 21 channel two was connected to the input to Flat Ribbon Cable Coil 25 and channel one was connected to Ferrite Core Inductive Transducer 26 through one of the two 23 Coaxial Test Probes and Leads. An AlphaLabs TriField Gauss Meter 27 was located either eight inches or twenty-two inches above Flat Ribbon Cable Coil 25 to measure the emitted magnetic flux from Flat Ribbon Cable Coil 25. Waveform results are illustrated in FIGS. 3 through 7 inclusive. FIGS. 6 and 7 used the water foot-bath controller with H-Bridge 28 instead of Signal Generator 22 to generate the different variations of waveforms. In these tests Ferrite Core Inductive Transducer 26 represents how the human body would 'see' the various waveforms. Each of the FIGS. 3 through 6 provides the test settings and results.

In Test 1, a 15V Peak-to-Peak 100 Hz sine wave was applied to Flat Ribbon Cable Coil 25 through Probes 23 and Input 24(see FIG. 3). In Test 2, a 15V Peak-to-Peak 100 Hz triangular wave was applied to Flat Ribbon Cable Coil 25 (see FIG. 4). In Test 3, a 15V Peak-to-Peak 100 Hz square wave was applied to Flat Ribbon Cable Coil 25 (see FIG. 5). In Test 4, water foot-bath controlled H-bridge 28 provided a Bipolar 24V Peak-to-Peak 100 Hz square wave applied to Flat Ribbon Cable Coil 25 through Probes 23 and Input 24 with Gauss Meter 27 placed 22" above Flat Ribbon Cable Coil 25 (see FIG. 6 top scope trace). In Test 5, water foot-bath H-bridge 28 provided a Unipolar 100 Hz square wave that was 12V Peak-to-Peak to Flat Ribbon Cable Coil 25 with Gauss Meter 27 placed 22" above Flat Ribbon Cable Coil 25 (see FIG. 6 bottom scope trace). The results of this testing are summarized in Table 1 below.

TABLE 1

| Test | Notes | Waveform | milliGauss | Distance | Volts |
|---|---|---|---|---|---|
| 1 | Tektronix FG503 Function Generator | Sine | 15 mG | 8 inches | 15 |

TABLE 1-continued

| Test | Notes | Waveform | milliGauss | Distance | Volts |
|---|---|---|---|---|---|
| 2 | Tektronix FG503 Function Generator | Triangular | 8 mG | 8 inches | 15 |
| 3 | Tektronix FG503 Function Generator | Square | 100 mG | 8 inches | 15 |
| 4 | Water Foot-Bath H-Bridge Controller | Bipolar Square | 90 mG | 22 inches | 24 |
| 5 | Water Foot-Bath H-Bridge Controller | Unipolar Square | 50 mG | 22 inches | 12 |

Of particular interest, not noted in Table 1, is how the body interprets, or sees, the various wave forms. The sine wave coupled to the body in FIG. 3 is perceived as a sine wave. The triangular wave coupled to the body in FIG. 4 is perceived as a square wave. And the square wave coupled to the body in FIG. 5 is perceived as positive and negative spikes at each transition. From these observations it was determined square waves as seen in FIG. 5 offered the best coupling with the body towards inducing cellular micro-currents and transference of specific vibrational frequencies. FIG. 6 indicated bipolar square wave pulses provided the best energy transfer, when compared to monopolar pulses observed in the existing electromagnetic therapy devices previously tested.

An additional Oscilloscope 21 measurement and capture was done with the H-Bridge PWM input being driven with an 880 Hz signal (30) while the direction input was driven at 50 Hz (29) to capture the resulting waveforms both at the Flat Ribbon Cable Coil Input 24 and at the Ferrite Core Inductive Transducer 26. This test resulted in the capture shown in FIG. 7. Channel 2 shows the unique waveform resulting from the exclusive-ORing of the two different frequencies through an H-Bridge. It shows two simultaneous frequencies as they are seen by the human body.

This lab testing validated the inventors' design to use an H-Bridge to drive the sleep mat flat coil with a bipolar square wave. By reversing the 12 VDC signal, the sleep mat flat coil sees an effective 24 volt signal, thus doubling the energy available to the coil when compared to a simple pulsed magnetic flux device that simply turns the current on and off. This also validated the effects of a 100 percent duty cycle. Also noted was the creation of odd harmonics of the fundamental frequencies that continued at decreasing amplitude, such that if the amplitude of the fundamental frequency was set to be within a safe range for the test subject, each odd harmonic was reduced to the appropriate safe range for its higher frequency. The results indicated generating bipolar square waves was the most efficient and safest energy wave transfer. In addition the testing further validated the efficacy of using the PWM input of the H-Bridge to add a second, higher frequency to support multiple simultaneous energy waves and further, that the human body would 'see' both frequencies and their subsequent harmonics.

In order to more fully understand the differences between the three different waveforms (sine, triangular, and square) driving the sleep mat flat coil, and to validate the earlier testing, additional testing was performed similar to that as illustrated in FIG. 2. The results of these tests are summarized in Table 2. In the first test, a 10V Peak-to-Peak sine wave signal at 55 Hz was applied to Flat Ribbon Cable Coil 25. In the second test a 10V Peak-to-Peak triangular wave signal at 55 Hz was applied to Flat Ribbon Cable Coil 25. In the third test a 10V Peak-to-Peak square wave signal at 55 Hz was applied to Flat Ribbon Cable Coil 25. In the fourth test the EnergyWave Therapy Device was set to deliver 55 Hz with Power Supply 8 adjusted to provide 10V Peak-to-Peak to Flat Ribbon Cable Coil 25. In the fifth test the EnergyWave Therapy Device was connected to Power Supply 8 at its full 12 volts DC rated level and connected to Flat Ribbon Cable Coil 25. In the sixth test the EnergyWave Therapy Device was connected to Power Supply 8 at its full 12 volts DC with Shorting Plug 13 installed to use PCB Copper Trace Coil 10 as seen in FIG. 1.

TABLE 2

| Test | Notes | Waveform | milliGauss | Distance | Volts |
|---|---|---|---|---|---|
| 1 | Tektronix FG503 Function Generator | Sine | 8 mG | 20 inches | 10 |
| 2 | Tektronix FG503 Function Generator | Triangular | 10 mG | 20 inches | 10 |
| 3 | Tektronix FG503 Function Generator | Bipolar Square | 35 mG | 20 inches | 10 |
| 4 | EnergyWave Therapy Device 120 | Bipolar Square | 3 mG | 20 inches | 10 |
| 5 | EnergyWave Therapy Device 120 | Bipolar Square | 70 mG | 20 inches | 12 |
| 6 | EnergyWave Therapy Device 120 with on board copper trace coil | Bipolar Square | 8.5 mG | 20 inches | 12 |

As testing of the sleep mat application proceeded, the inventors determined the EnergyWave Therapy Device needed to be modified to generate healing frequencies which emulated natural Circadian rhythms in order to improve the sleep cycles of the test subjects and further reduce any possibility of frequency fatigue, noted to occur when a person was exposed to a single frequency for extended (usually years) of time. During sleep REM (Rapid Eye Movement) cycles, or the dream cycles of sleep, the body does most of its own natural healing. Infants spend most of their sleep in REM cycles. Sleep Stages 3 and 4, referred to as deep sleep, is when the body experiences its physical restorative and regenerative sleep. As people age they spend progressively less time in both natural healing REM sleep and deep sleep. By supporting the body's natural Circadian rhythms, the apparatus can increase the time spent in both healing REM cycles and deep sleep, and can add specific healing frequencies to boost the body's healing processes. The result is a natural sleep cycle attained through brainwave entrainment with magnetic flux emitted by coil 25.

The sweep mode noted earlier for the foot-bath apparatus had been used by some test subjects for what they referred to as 'power napping'. In this method of application, the test subjects would set the EnergyWave Therapy Device to sweep mode, which ran a twenty-five minute cycle through the ten frequencies from 5.5 Hz to 55 Hz, then the test subjects would then take a fifty minute nap, allowing the EnergyWave Therapy Device to go through the cycle twice. All the test subjects who used this 'power nap' mode reported awakening from the fifty minute nap feeling fully rested and energized, as though they had slept for a much longer period of time.

Additionally, some test subjects would sleep with the EnergyWave Therapy Device on 5.5 Hz then step it up to 55 Hz when awakened in the morning by their alarm clock, since the 55 Hz had a more energizing effect. It should also be noted for the sleep-mat application, the 880 Hz PWM input had to be disabled, as adding it to the sleep-mat created a higher frequency that interrupted sleep. To this end a toggle switch was added to the crystal controlled CMOS based EnergyWave Therapy Device to enable or disable the 880 Hz PWM input to the H-Bridge. Some sleep-mat users found it helpful to turn the 880 Hz PWM input on in the morning to add an energizing effect. These experiences and other insights led to the idea of creating preset programs to support various sleeping, napping and therapeutic application. In order to accomplish these new features the current CMOS implementation needed to be converted to a microcontroller based EnergyWave Therapy Device to allow for creating the multiple preset programs and a wider range of frequencies, which would also allow for addressing even more symptoms.

It was determined that Microchip's family of industrial microcontrollers were well suited to the task and work began on developing a new design, schematics, Printed Circuit Boards (PCBs) and firmware to operate the new microcontroller. A new user interface was required and the simple flat ribbon cable coil gave way to an even simpler, less expensive idea of incorporating the coil as copper traces on both sides of the perimeter of the PCB hosting the new circuit. The new EnergyWave Therapy Device needed to continue to support the external sleep mat flat coil, water foot-bath energy delivery mechanism described above and other modalities of delivering vibrational energies to a test subject.

Additional embodiments of the apparatus were created to be used during massage or physical therapy to reduce pain and relax muscles. Another embodiment was created to be used as a handheld device to reduce pain and inflammation and relax muscles. Another embodiment was created to reduce wrinkles in the skin, reduce scarring, and assist in reducing acne or other skin problems.

The inventors realized an effective EnergyWave Therapy Device must use a Fibonacci number quartz crystal as its base timing element. While quartz crystals have been used for years for their inherent stability and accuracy as a timing element in many applications from radios to computers, they have an even longer history of being used in natural healing that predates the electro-industrial age. Shamans, spiritual healers, and esoteric practitioners have used, and continue to use, crystals in various forms for a multitude of purposes, but the basic quartz crystal has been used most frequently as a tool to heal the sick, ostensibly by aligning the natural healing energies of the quartz crystal with the ailing or afflicted portion of the person or animal until such time as the misaligned energies in the afflicted person or animal were brought back into harmony with the whole.

In addition to the basic timing element being a quartz crystal, the appropriate fundamental frequency must be as close as possible to a Fibonacci number as presented above. The inventors first used a color-burst crystal, common in older color televisions, being the frequency of 3,579,545 Hz, which was slightly more than 1% from the natural Fibonacci number of 3,524,578. Testing with the crystal controlled CMOS water foot-bath embodiment of the EnergyWave Therapy Device was successful in proving several critical factors, sufficient to confirm that a quartz crystal with a fundamental frequency as close as possible to a Fibonacci number was critical to the effectiveness of the apparatus.

To validate this hypothesis, a second version of the EnergyWave Therapy Device was created using a standard '555' timer IC with a resistor/capacitor based frequency generator. While such a device was able to produce the same frequencies as the crystal controlled version, the results of the testing were not as positive as with the first embodiment using a color burst quartz crystal. Subsequently, another test device was built using a quartz crystal with a frequency of 3,600,000 Hz which produced frequencies that were equally as close to the well noted Rife frequencies as provided by the color burst crystal, but the fundamental frequency was further away from a natural Fibonacci number. Again the test subjects reported less positive responses than with the color burst crystal version. A third embodiment of the EnergyWave Therapy Device was created using the aforementioned industrial microcontroller to allow the generation of more frequencies and to emulate the natural Circadian rhythms of life. This third embodiment relied upon the internal resistor/capacitor timing elements to form the fundament frequencies and again the device failed to be as effective in achieving the desired results as when the color burst crystal was used.

In these blind tests, test subjects did not know whether their EnergyWave Therapy Device used a quartz crystal or not, and if it did use a quartz crystal, which fundamental frequency it was. Test subjects reported a higher degree of irritation and discomfort and less feeling of general wellness with the non-quartz crystal based devices. In further testing using quartz crystals that were not as close to Fibonacci numbers, the test subjects in the blind tests reported less effectiveness of the device, more difficulty falling asleep, and awaking feeling more irritable than usual. Thus it became apparent for the EnergyWave Therapy Device to be effective the generated vibrational energy had to be through the use of a quartz crystal whose fundamental frequency is as close as possible to a natural Fibonacci number. In the current preferred embodiment of this invention the selected crystal has a fundamental frequency of 15,000,000 Hz which is less than 0.5% from the Fibonacci number 14,930,352, and is referred to as a Fibonacci Number Quartz Crystal 4 in FIG. 1. Subsequent testing of the new embodiment with the 15,000,000 Hz quartz crystal and microcontroller have demonstrated the healing and relaxing effects to be even more prominent than with the earlier CMOS EnergyWave Therapy Device using the Color Burst crystal.

Another discovery deals with the use of low power bipolar magnetic fields, in the non-ionizing extremely low frequency range of the EM spectrum, through the use of a simple copper trace coil integrated into the printed circuit board (PCB) containing the main embodiment of this invention. While multiple patents have been granted using a coil on a PCB, or even a flexible PCB, this is the first occurrence of using such a coil to emit an extremely low frequency magnetic wave for healing purposes. In the related patents the coil was used to measure inductance, not to emit ELF EMF flux, hence this is a novel and non-obvious method of applying an existing idea.

There also exists the need to invoke a biological response in the test subject without causing any harm. The criticality of this is represented in the 1987 World Health Organization's report on the safe levels of such fields. Consequently, the embodiment of this invention operates on a very low level of magnetic flux, below 100 milliGauss at 3 Hz at the prescribed distance between the user and the emitter, being equivalent to 0.01 milliTeslas at 3 Hz. Therefore, this device is referred to as a homeopathic device, as such levels are more than twenty times lower than the thresholds necessary to cause any observable biological effects reported by the World Health Organization as occurring from 0.5 to 5 milliTeslas at 3 Hz, and more than a million times lower than 1 to 10 Teslas at 3 Hz reported to be hazardous levels. Yet through extensive testing this apparatus has proven to be effective in improving sleep, reducing pain and promoting natural healing.

Further safety testing was conducted with Guidant Corporation implantable cardioverter defibrillators (ICDs) and implantable cardiac resynchronization therapy pacemakers (CRT-Ps) to determine if the apparatus would interfere with their proper operation, or trigger false events causing unnecessary defibrillation shocks to a patient. ICDs and CRT-Ps are designed to meet the established industry standards for sensitivity to home and industrial EMI. The Guidant Corporation devices are designed to operate properly with EMI from 0.1 Hz to 3,000 Hz with the magnetic flux not exceeding 2 Gauss, which is twenty times greater than the measured bipolar magnetic flux fields emitted by the EnergyWave Therapy Device. The EnergyWave Therapy Device was operated at all supported frequencies and with all available external adapters with the ICDs and CRT-Ps abutted to the apparatus and in no case was a false event triggered, nor was the operation of the ICD or CRT-P interrupted. In all test cases the emitted bipolar magnetic flux field was below the Guidant Corporation's EMI thresholds. This testing was critical as the EnergyWave Therapy Device operates in the range of frequencies monitored by the ICDs and CRT-Ps to manage cardio pacing and prevent cardio-fibrillations. During the testing audio alarms were enabled in the ICDs and CRT-Ps and telemetry monitoring was used. While the apparatus did interfere with the telemetry pick-up wand when placed too close, the ICDs and CRT-Ps continuously operated safely. This testing was with the preferred embodiment of the EnergyWave Therapy Device in direct contact with the ICDs and CRT-Ps, which is impossible to achieve in vivo, and therefore there is little possibility of interference in actual application.

BRIEF SUMMARY OF THE INVENTION

This is a new invention which is safer, simpler to use, less invasive into a user's daily routine and provides a lower cost solution to existing pulsed magnetic field and related vibrational electromagnetic therapy devices. This invention (apparatus) is referred to as an EnergyWave Therapy Device to distinguish it from existing electromagnetic therapy devices. It operates non-invasively on a homeopathic level to improve sleep, encourage natural healing and reduce pain, swelling, and general discomfort. This is accomplished through different embodiments of the apparatus all of which generate Multiple Simultaneous Extremely Low Frequency (MSELF) energy waves which may be any combination of Alternating Polarity Magnetic Fields (APMF), narrowband near-coherent long-wavelength (580 nm to 980 nm) light emitting diodes (LEDs), or electrical vibrations transmitted through the medium of water using carbon rod electrodes. The MSELF vibrations are derived from a quartz crystal with a fundamental frequency less than one-half of one percent from a natural Fibonacci Number. The apparatus utilizes firmware operating in a microcontroller containing predefined, user selectable therapy programs either emulating natural Circadian Rhythms for sleep and rest, or other therapeutic programs, all of which contain Electromagnetic Field (EMF) dose limitations to prevent any possible overexposure. The microcontroller is also clocked at the same fundamental frequency generated by the Fibonacci Number Quartz Crystal. Additionally, the apparatus's unique application of an H-Bridge configuration power-driver with Pulse Width Modulation (PWM) capabilities supports a novel approach to supply two simultaneous therapeutic frequencies to either a copper-trace coil emitter integrated on the main Printed Circuit Board (PCB) or optional external energy emitters. The result is a more effective, lower energy, safer, lower cost, simpler to use, non-invasive, multi-modal, EnergyWave Therapy Device.

The EnergyWave Therapy Device (apparatus) was developed for persons with sleep disorders, muscle and joint stiffness, excessive swelling and pain. The apparatus provides vibrational homeopathic therapy delivered in its unique bipolar magnetic EnergyWave format. These healing energy waves support the body's own natural Circadian rhythms occurring during normal sleep and waking periods.

The apparatus may be used during sleeping, napping or daytime rest and relaxation periods to rejuvenate and boost the body's healing cycles. When used during massage therapy it helps a person relax, loosen tight muscles and enhances the overall experience by placing both the massage practitioner and patient inside the natural healing energy field.

BRIEF DESCRIPTION OF DRAWINGS

FIG. 6 shows the oscilloscope capture of the comparison of the resultant bipolar verses a unipolar generated square waves.

DETAILED DESCRIPTION

Figure 1:
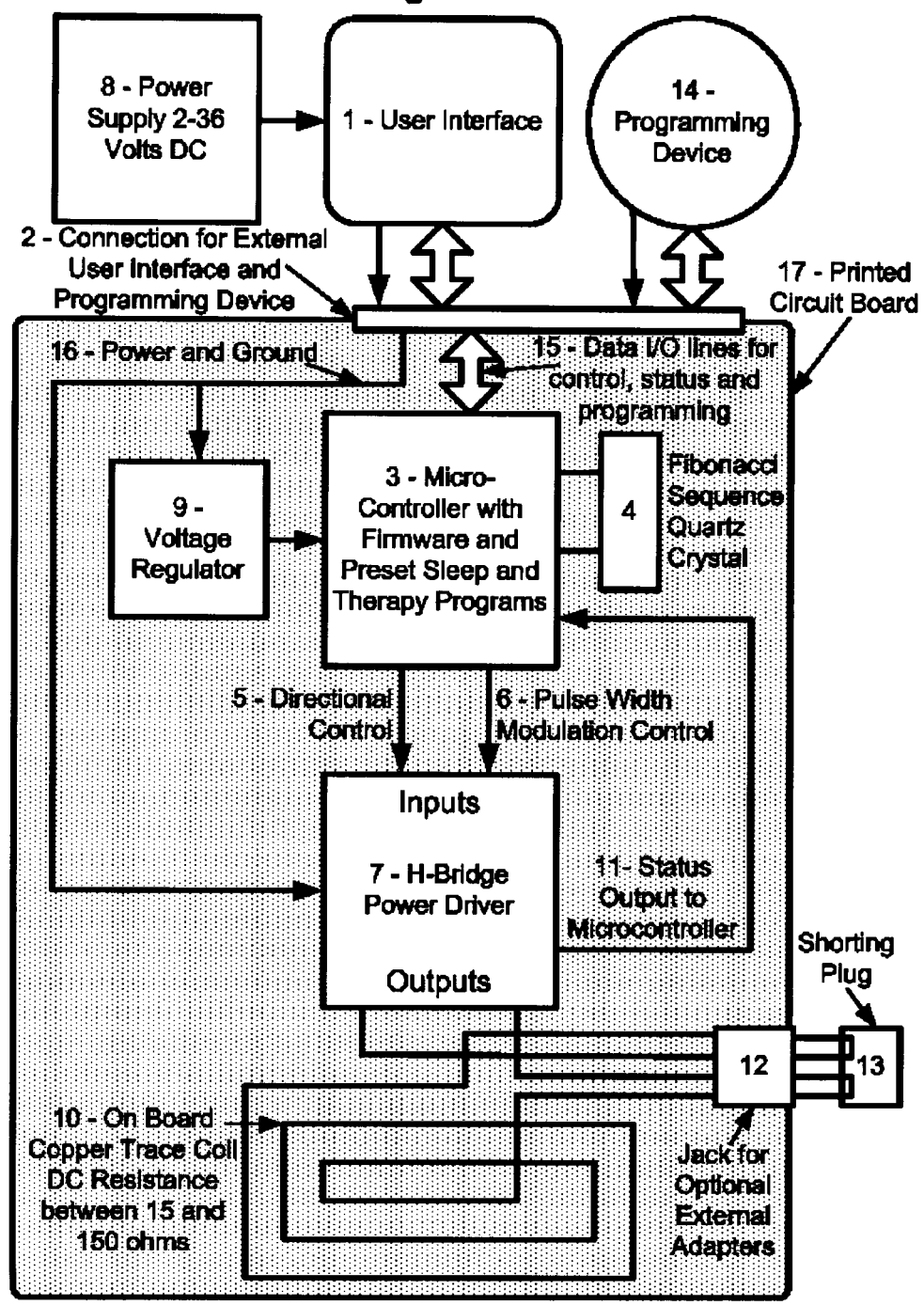
FIG. 1 is a block diagram of the embodiment of the invention, referred to as an EnergyWave Therapy Device, showing the major components their connections and functions.
Figure 2:
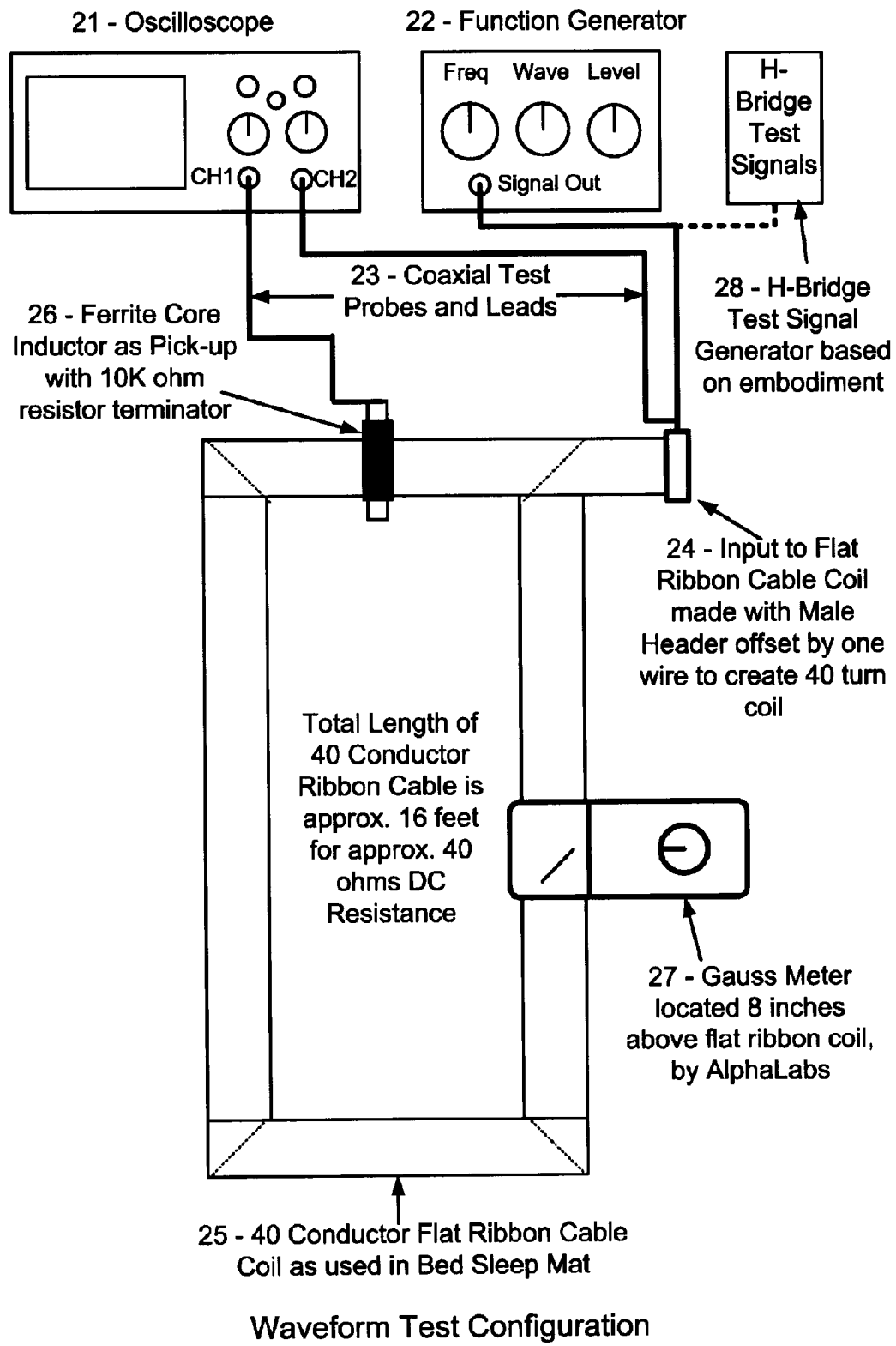
FIG. 2 depicts the test configuration for generating and comparing the various waveforms and resultant magnetic flux measurements.
Figure 3:
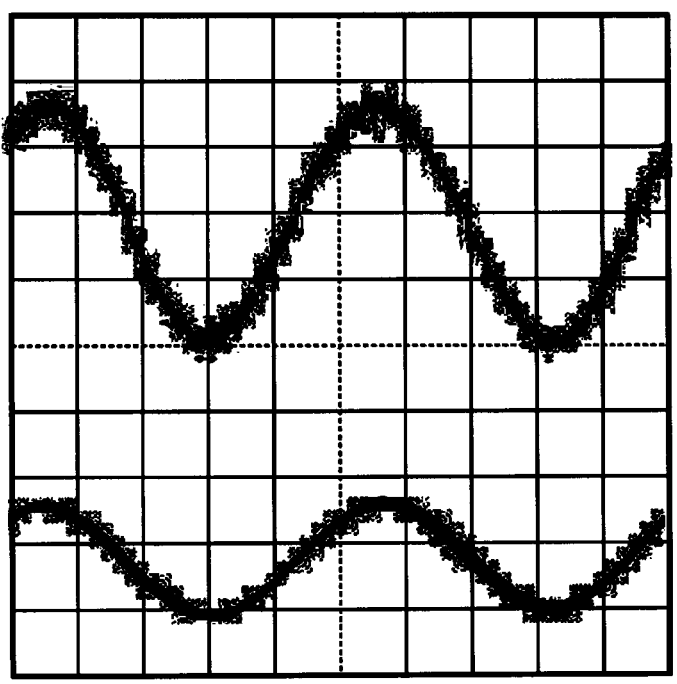
FIG. 3 shows the oscilloscope capture of a sinusoidal wave and its resultant duplicate waveform in the test coil.
Figure 4:
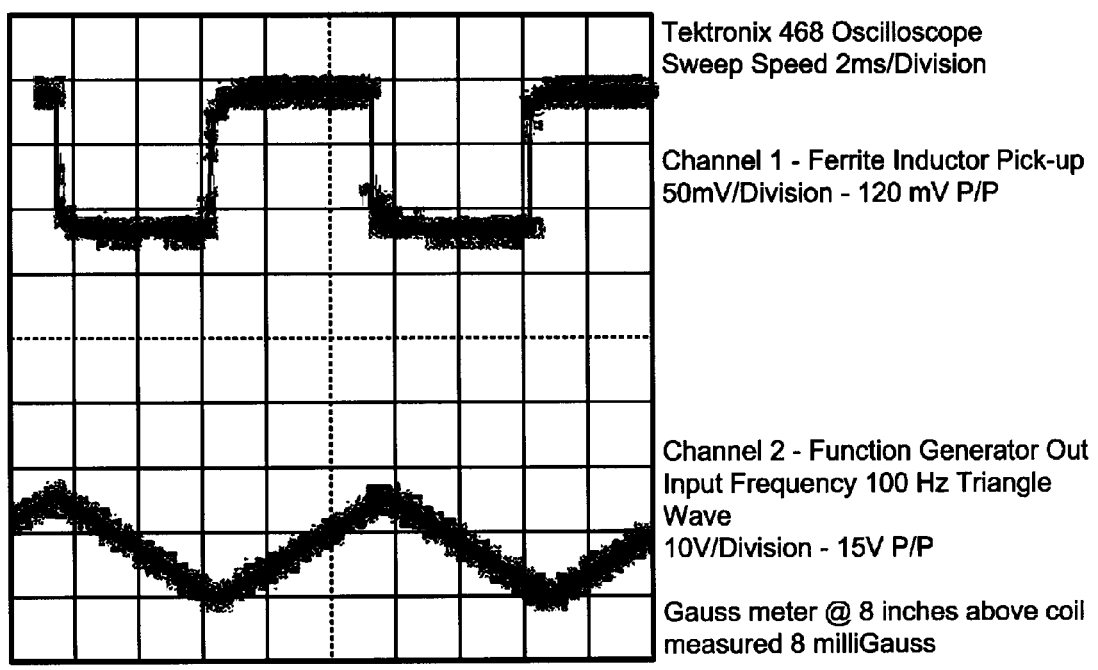
FIG. 4 shows the oscilloscope capture of a triangular wave and its resultant square waveform in the test coil.
Figure 5:
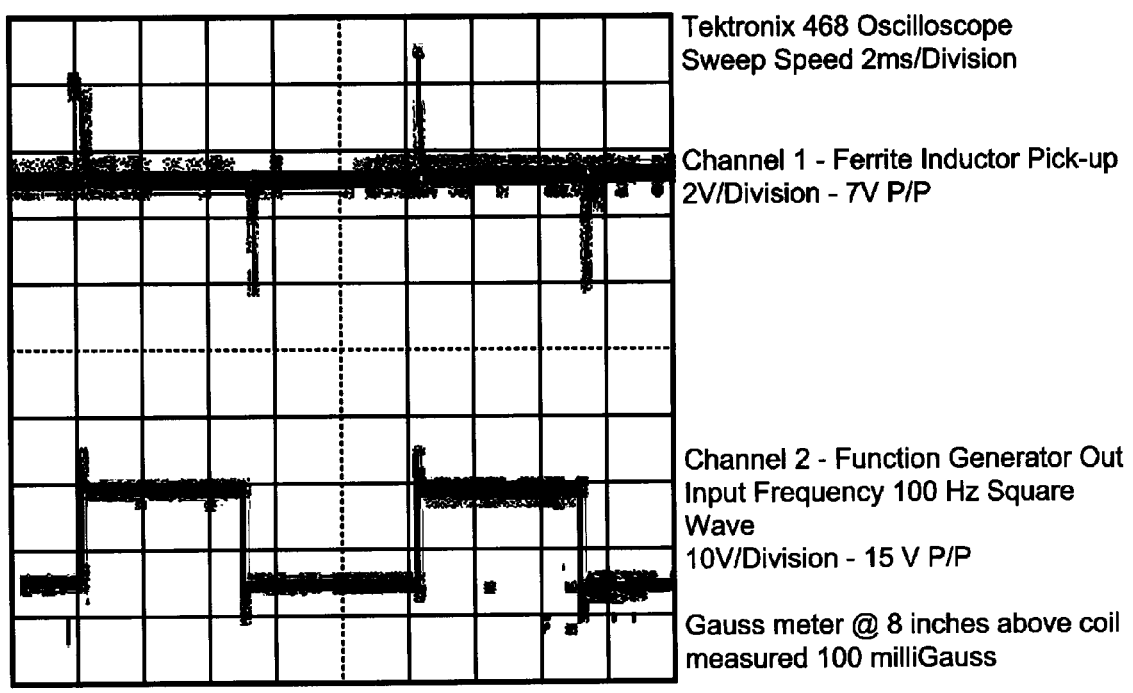
FIG. 5 shows the oscilloscope capture of a square wave and its resultant bipolar pulse waveform in the test coil.
Figure 7:
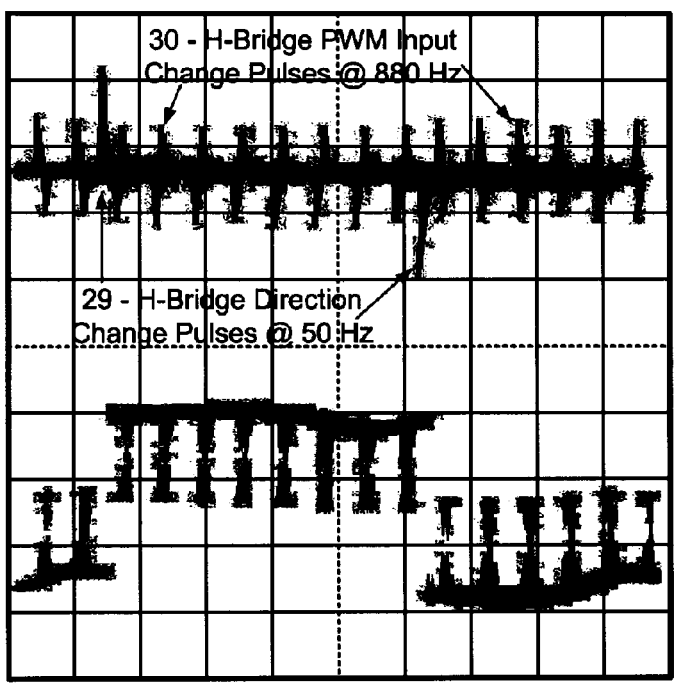
FIG. 7 shows the oscilloscope capture of the H-Bridge operating with two simultaneous frequencies and the resultant waveform in the test coil.
Figure 12:
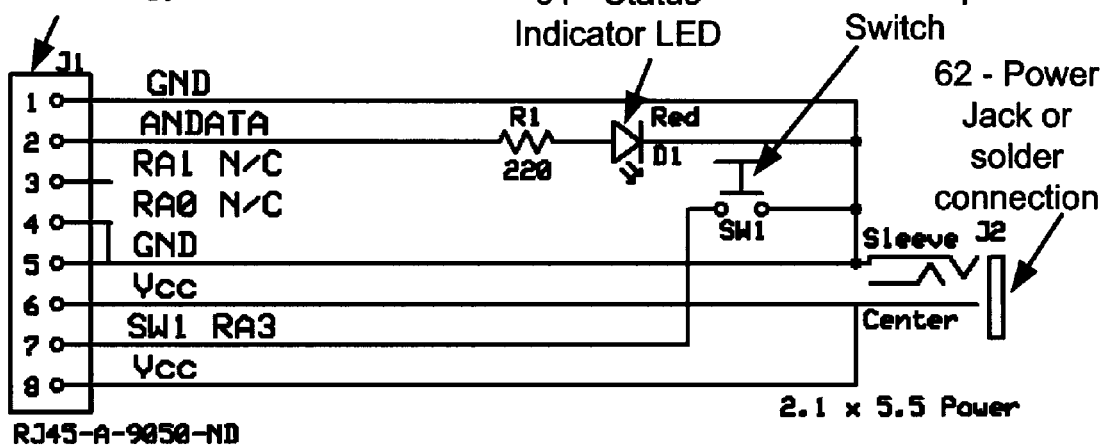
FIG. 12 is a schematic diagram of a single LED and single switch user interface PCB.
Figure 13:
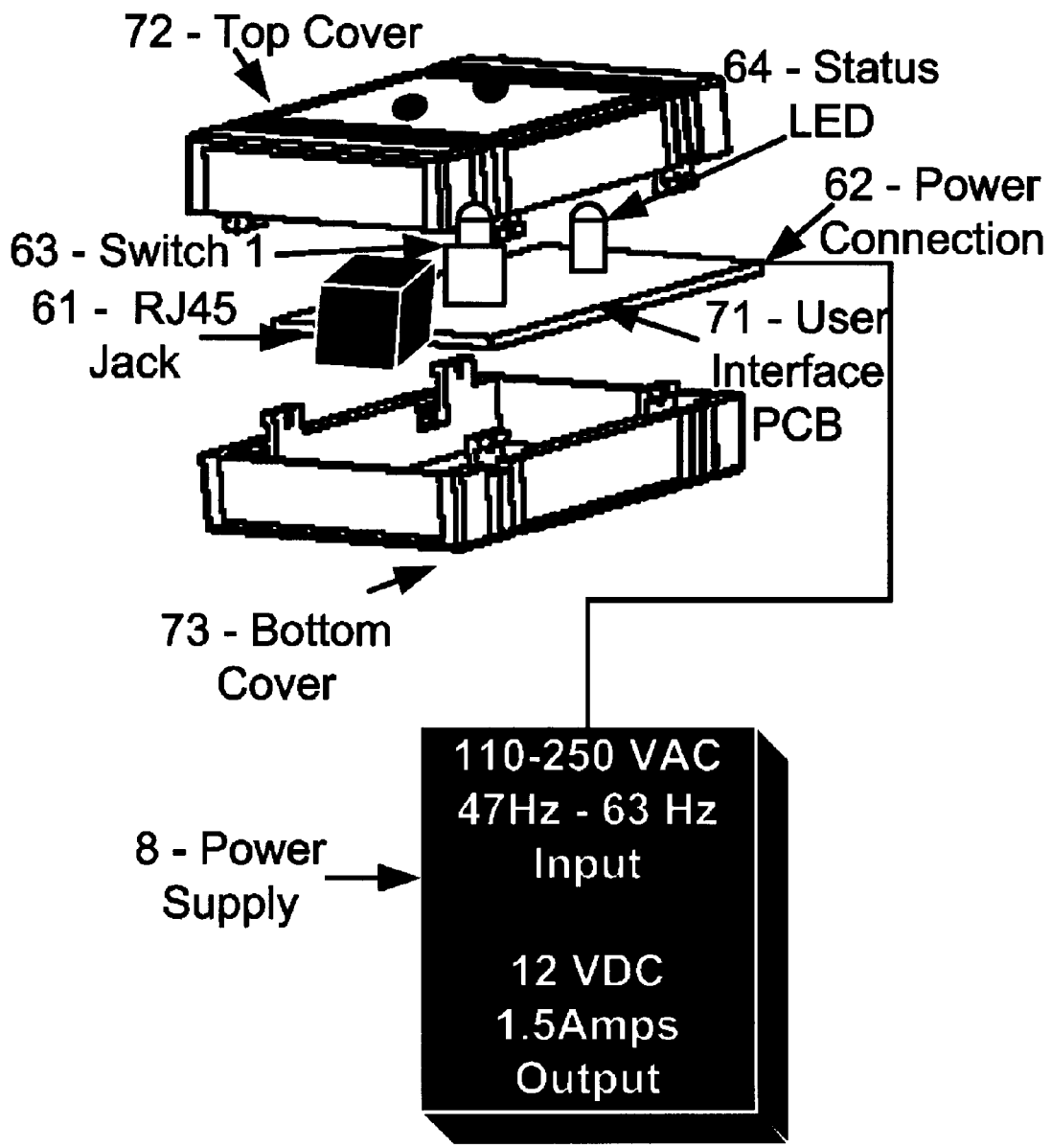
FIG. 13 is an assembly drawing for the user interface PCB depicted in FIG. 12.

The embodiment of this invention is referred to as the EnergyWave Therapy Device 120, as depicted in FIG. 1, being a block diagram of the preferred embodiment showing the components and their connections. The User Interface 1 and the Programming Device 14 are connected to the Printed Circuit Board (PCB) 17 through the Connection 2. The Power Supply 8 supplies power and ground to User Interface 1, which is then forwarded to PCB 17 through Connection 2 and to individual components on Printed Circuit Board 17 via connections power and ground connections labeled 16. Programming Device 14 also provides power and ground to PCB 17 through Connection 2 for use during the programming of Microcontroller 3. Programming Device 14 is used during the assembly of the apparatus for programming Microcontroller 3 with the desired firmware to enable its operation. Programming Device 14 is selected based upon the requirements for the selected Microcontroller 3. Additionally, Programming Device 14 may be used post assembly for upgrading the firmware of Microcontroller 3, or for upgrading or adding new preset programs to Microcontroller 3. User Interface 1 can take the form of many different embodiments, depending upon the level of functionality desired with the subsequent cost each embodiment incurs. Two different embodiments of User Interface 1 are documented as depicted in FIG. 12 through 13 inclusive, showing both a schematic diagram and assembly for each. These are discussed in detail later. Sufficient for now is that each User Interface 1 has the capability of displaying information to the user and the capability to support the user sending information to Microcontroller 3 via Connection 2.

The remaining components are hosted on the Printed Circuit Board (PCB) 17. Connection 2 contains the Data Input/Output (I/O) lines 15, and connections for power and ground 16. In the preferred embodiment Connection 2 is an 8 conductor modular RJ-45 Jack. Data I/O lines 15 includes two output lines from Microcontroller 3 used to send display information to User Interface 1, and two input lines to Microcontroller 3 used to receive user input from User Interface 1.

Microcontroller 3 receives its power through the Voltage Regulator 9 that keeps the voltage presented to Microcontroller 3 within the prescribed limits established by the manufacturer of Microcontroller 3. In the preferred embodiment Microcontroller 3 is a Microchip 16F688, although any microcontroller with adequate memory and I/O lines may be used. The Fibonacci Number Quartz Crystal (or simply Crystal hereafter) 4, is quartz crystal having a fundamental frequency as close as possible to a natural Fibonacci number. In this embodiment Crystal 4 has a selected fundamental frequency of 15,000,000 Hertz, or cycles per second.

Microcontroller 3 has up to three output lines that connect to the selected H-Bridge Power Driver 7, depending upon which H-Bridge is used. In the preferred embodiment a DMOS H-Bridge is used that only requires one Direction Control 5 line, whereas in the alternative lower cost embodiment depicted in FIGS. 19 and 20 H-Bridge 7 requires two Direction Control lines, 5a and 5b. Both H-bridges require one Pulse Width Modulation (PWM) 6 control line, referred to as an Output Enable in the lower cost alternative. H-Bridge 7 is powered directly from the external Power Supply 8 via User Interface 1 and through Connection 2. In the preferred embodiment H-Bridge 7 provides a Status Output 11 to Microcontroller 3 that indicates an open condition across the outputs of H-Bridge 7, or a short between one of the outputs to either power or ground.

In the preferred embodiment PCB 17 includes an On Board Copper Trace Coil 10, with a DC resistance of between 15 ohms and 1,000 ohms. This is nominally designed to be between 25 to 75 ohms. Copper Trace Coil 10 consists of a two contiguous copper traces, or runs, on the perimeter of PCB 17. The traces are from between 0.005 inches to 0.020 inches in width and are spaced from 0.005 to 0.025 inches between each trace. Each top and bottom trace coil is approximately equal in length with the top and bottom copper traces offset from one another, such that a copper trace on the top surface of PCB 17 is not directly over a copper trace on the bottom of PCB 17. The two coils are connected in series in such a manner as to ensure that the current flow is in the same direction when PCB 17 is viewed from the top.

The power driving Outputs depicted at the bottom of H-Bridge 7 are connected to the Optional External Adapters Jack (Adapter Jack) 12. In the preferred embodiment Adapter Jack 12 is a 6 conductor modular RJ-11 or RJ-25 jack. In this configuration, H-Bridge 7 Outputs are connected to the center two pins (pins 3 and 4) and the outer two pins (pins 1 and 6) such that pins 1 and 3 are connected to one output and pins 4 and 6 are connected to the other output of H-Bridge 7. The remaining two pins of Adapter jack 12 are connected to the ends of On Board Copper Trace Coil 10. If no external adapter is used a Shorting Plug 13 is installed into Adapter Jack 12, connecting the outputs of H-Bridge 7 to the On Board Copper Trace Coil 10 to allow current to flow and thereby generate the desired bipolar magnetic flux field.

Figure 8:
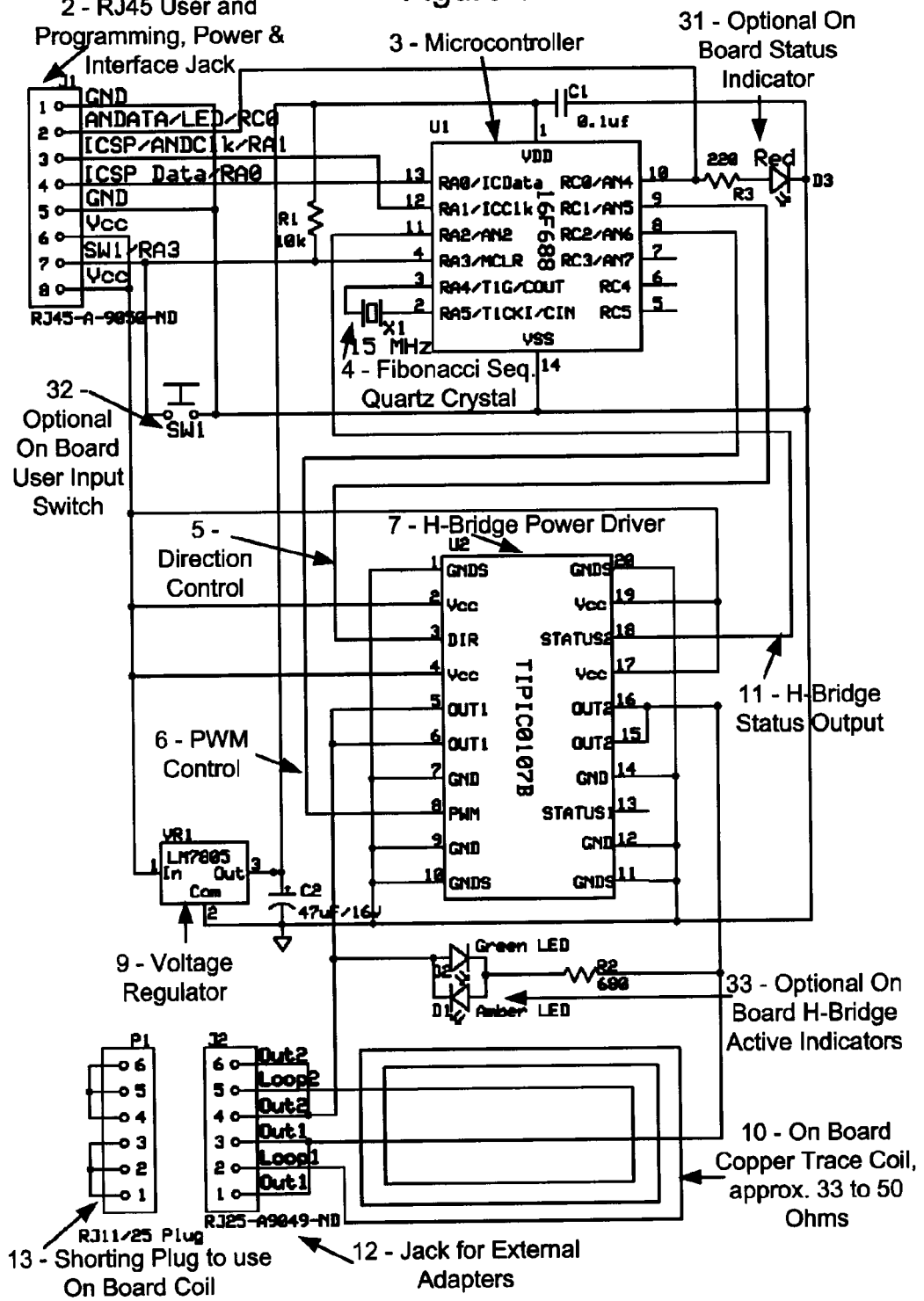
FIG. 8 is a schematic diagram of the preferred embodiment of the EnergyWave Therapy Device.

FIG. 8 shows the schematic diagram of the preferred embodiment of the apparatus. In FIG. 8 there are three optional components depicted for applications without an external User Interface 1. These are Optional On Board Status Indicator 31, Optional On Board User Input Switch 32 and Optional On Board H-Bridge Active Indicators 33. If no User Interface 1 is desired, then these optional components may be added to PCB 17 to allow operation without external User Interface 1. In this configuration, Power Supply 8 will simply connect to Connection 2 and provide only power and ground on the prescribed pins.

Figure 9:
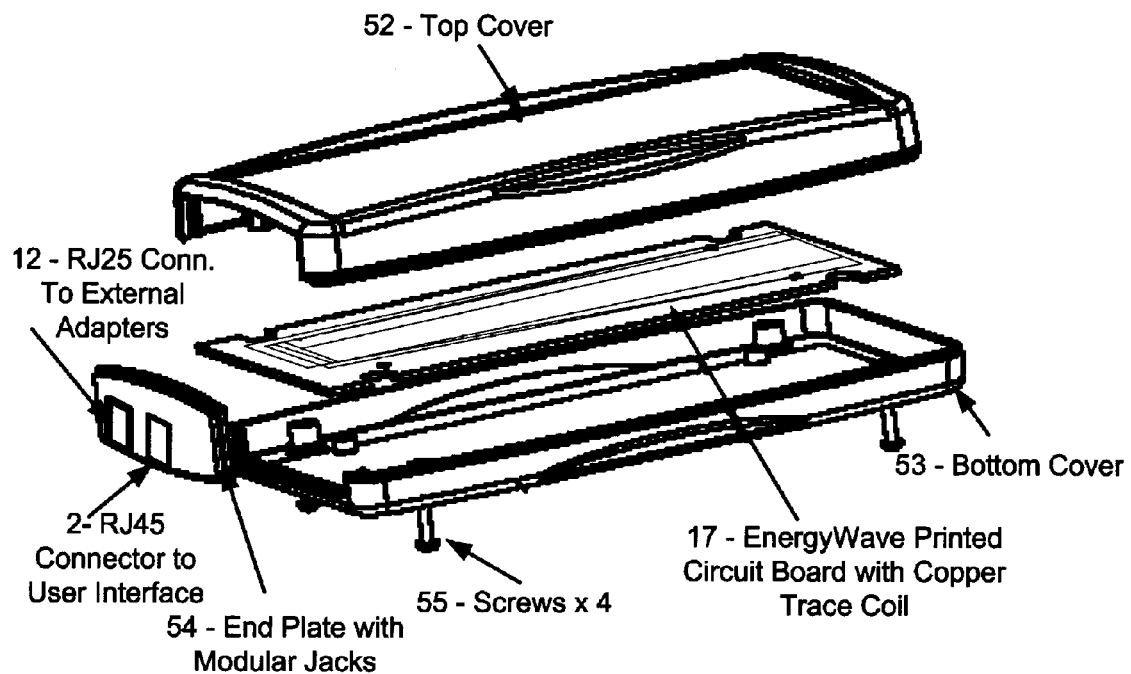
FIG. 9 is an assembly drawing of the preferred embodiment of the EnergyWave Therapy Device.

FIG. 9 depicts the final assembly of the preferred embodiment where PCB 17 is installed into a plastic case with Top Cover 52 and Bottom Cover 53 held together by four Screws 55. End Plate 54 is cut out to allow access to Connector 2 and Adapter jack 12.

Overview of Software Flowchart and Tables

Figure 10:
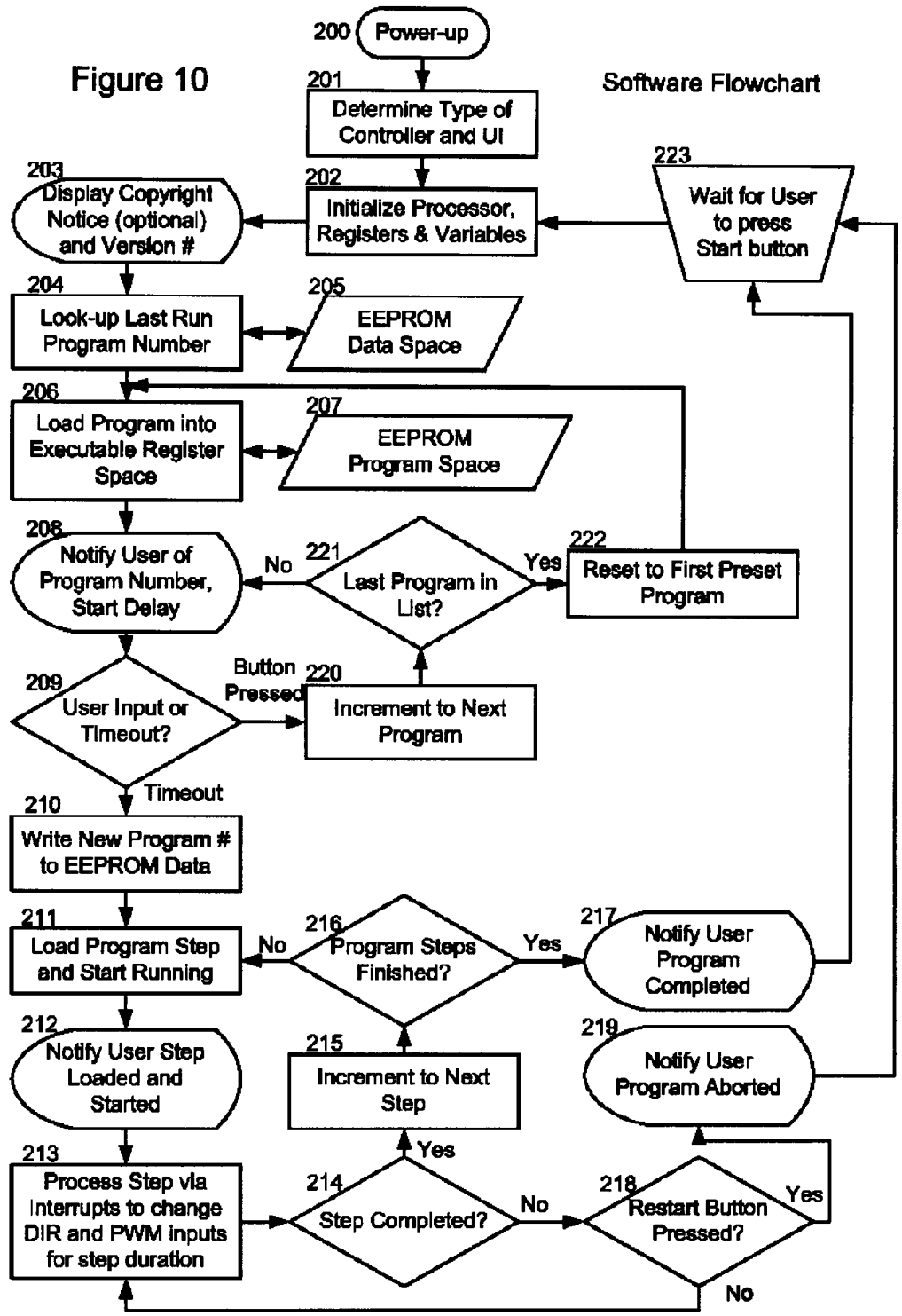
FIG. 10 is the software flowchart for the firmware resident in the microcontroller.
Figure 11:
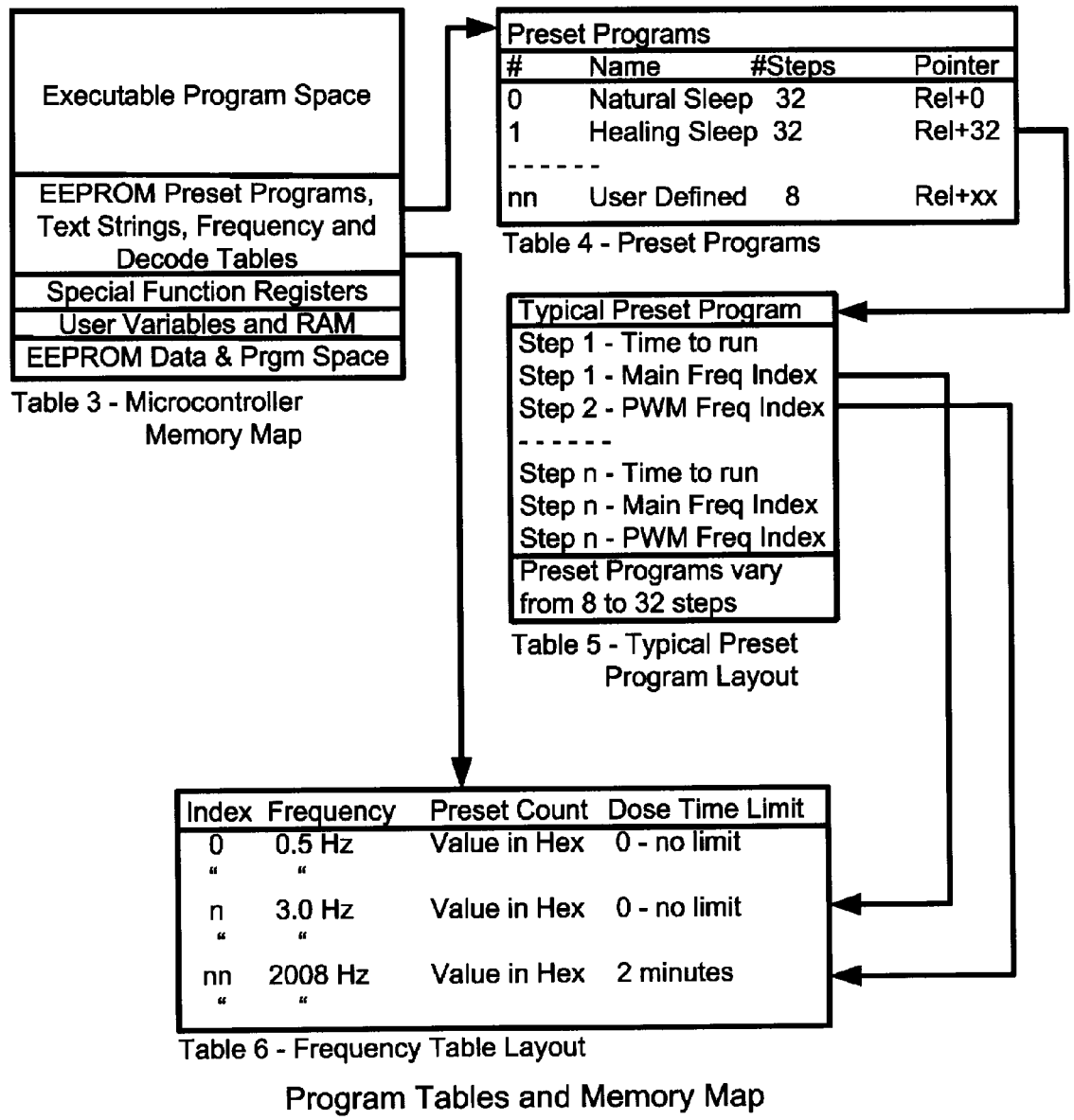
FIG. 11 depicts the microcontroller memory map and software tables essential for processing the preset programs.

FIG. 10 is a software flowchart showing the overall operation of the EnergyWave Therapy Device based upon table driven data as shown in FIG. 11. All timings for Microcontroller 3 are derived from Crystal 4 and subsequently each desired frequency to be emitted by H-Bridge 7 is defined in Table 6 of FIG. 11. The apparatus may have as many preset programs as there is sufficient memory to accommodate and as many as may be manipulated easily by the user through the chosen User Interface 1. Generally, the single LED user interface is used for up to 6, but preferably 4 programs; the single digit seven segment user interface is used for up to 16, but preferably 8 programs; the two digit, two switch user interface is used for up to 100 programs and individual frequencies, but preferably 22 programs and 64 individual frequencies; the single character alphanumeric display two switch user interface is used for up to 100 programs and individual frequencies, but preferably 22 programs and 64 individual frequencies.

Refer to FIGS. 10 and 11 for the following software flow overview. The software functions are numbered 200 through 223 inclusively and are represented in the following discussion within parenthesis for ease of reference.

When the apparatus is powered up (200) Microcontroller 3 must initialize (201) its ports. The software completes its initialization process (202) and clears all registers and memory for variables. The last digit of the version is flashed on the LED on User Interface 1 and there is no copyright notice displayed.

The software then executes a Data EEPROM read (204) where non-volatile data (205) is stored from previous sessions to find which program was last run. The program index is read and validated to be in range of allowed programs for the controller connected and the program is copied (206) from Program EEPROM memory (207) to the general purpose registers for execution.

The software then displays the program number or name (208), depending upon User Interface 1 that is attached and a five second delay is started. During the five second delay (209) the user may press Switch 1 to step to the next program (220) or do nothing until the timeout. If the user presses Switch 1 (220) the program counter is incremented and tested (221) to determine if the last program in Table 4 in FIG. 11 has been exceeded. If the program index exceeds the last entry the program index is reset to zero in Table 4 (222) and the first program is loaded (206) into register space and the program name or number is displayed to the user (208) and the five second timer is restarted (209).

Upon the five second timer expiring (210) the program index number is written back out to EEPROM Data for retrieval on the next start-up. The first step in the selected program from Table 5 in FIG. 11 is loaded into the current step registers (211) and the user is notified the program step is loaded and the program begins running (212).

Each program can contain any number of steps. In the preferred embodiment the programs have either eight, sixteen or thirty-two steps (see Table 3 in FIG. 11). The Program Table 4 provides a name and number for each program, depending upon the User Interface 1 that is used, and a pointer to where the actual program steps are stored. The actual program steps have three entries each (see Table 5 in FIG. 11). First is the time for how long this step is to execute. Second is the main frequency to be sent to the H-Bridge 7's Direction Input 5. The third entry is the secondary frequency to be sent to the H-Bridge 7's PWM input 6. Once the program begins executing the first step a 125 microsecond hardware interrupt timer is used to increment an internal timer for determining when the step time is completed. A second hardware interrupt timer is used with the preset hexadecimal values stored in Table 6 to preload the timer/counter with the appropriate value for the selected frequency. If two frequencies are specified (one for Direction 5 input and one for PWM 6 input) then a second software timer is enable to track the slower Direction 5 input frequency and the hardware interrupt timer is used for the higher PWM frequency.

The software in Microcontroller 3 operates using the interrupts (213) from the various hardware interrupts and software based timers and user switch inputs to process each step to completion. The 125 microsecond hardware interrupt timer is also used for debouncing the switch inputs and for clocking display data to the shift registers for the User Interfaces that have one or more digits or characters.

When a program step software time-out (214) occurs the time for the step is decremented and tested to see if this step is completed. If the step is completed the software increments to the next step (215) in the preset program and tests to see if the last step has been run (216). If more steps need to be run then the next step is loaded (211) and the process continues until the last step in the preset program is completed. When the last step is completed the user is notified the program has completed (217) and the software waits (223) for the use to press Switch 1 to restart (202).

If the user presses Switch 1 (218) while the program is executing, the software interprets that as an abort request and stops the current preset program from running and notifies the user the program has been halted (219). The software waits (223) for the user to press Switch 1 again to restart (202). Alternatively, pressing Switch 1 can be used to increment the preset program to the next step for testing purposes.

User Interfaces

FIGS. 12 through 13 inclusive cover the preferred embodiments for User Interface 1. Each version uses the same Connector 61 to connect to PCB 17's Connector 2 to provide power and ground and supports the ability to notify the user and to allow the user to send switch presses to Microcontroller 3. Jack 61 connects the User Interface 1 to the PCB 17. Status Indicator 64 is an LED that can be flashed by the microcontroller 3 in various formats to signal information to the user. User Input Switch 63 is a normally open momentary push button switch to all the user to signal microcontroller 3. Power Jack 62 accepts the DC power input to operate the apparatus.

It is anticipated that for most users the availability of 8 programs will cover most conditions. Further, the preset programs have been designed to take the guess work out of using the apparatus.

External Attachments

The preferred embodiment of the apparatus supports both an On Board Copper Trace Coil 10 and an Adapter jack 12 for external attachments. Included for example are three commonly used external EnergyWave attachments.

Figure 14:
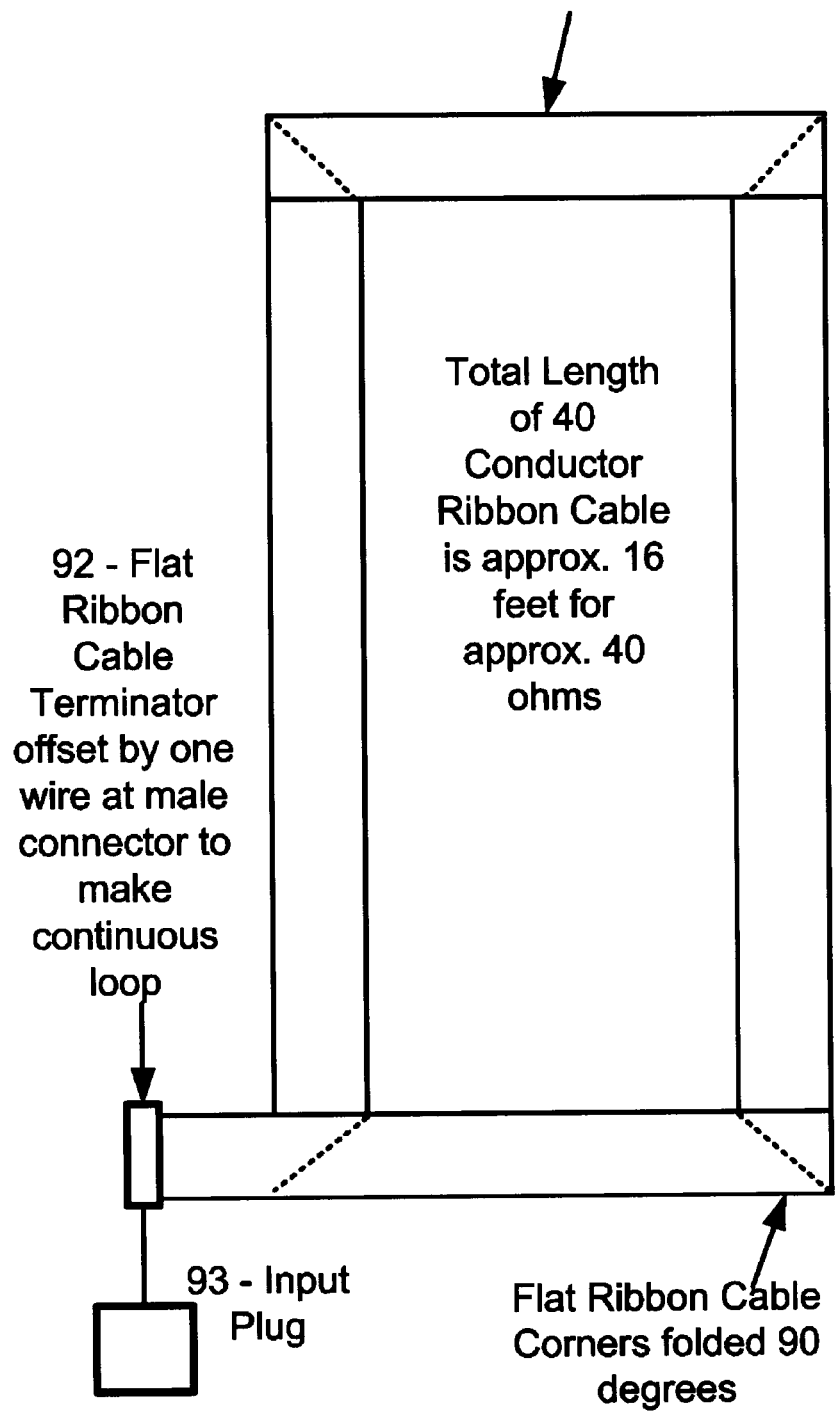
FIG. 14 shows a typical sleep mat coil as an external attachment to the Energy Wave Therapy Device constructed from 40 conductor flat ribbon cable.
Figure 15:
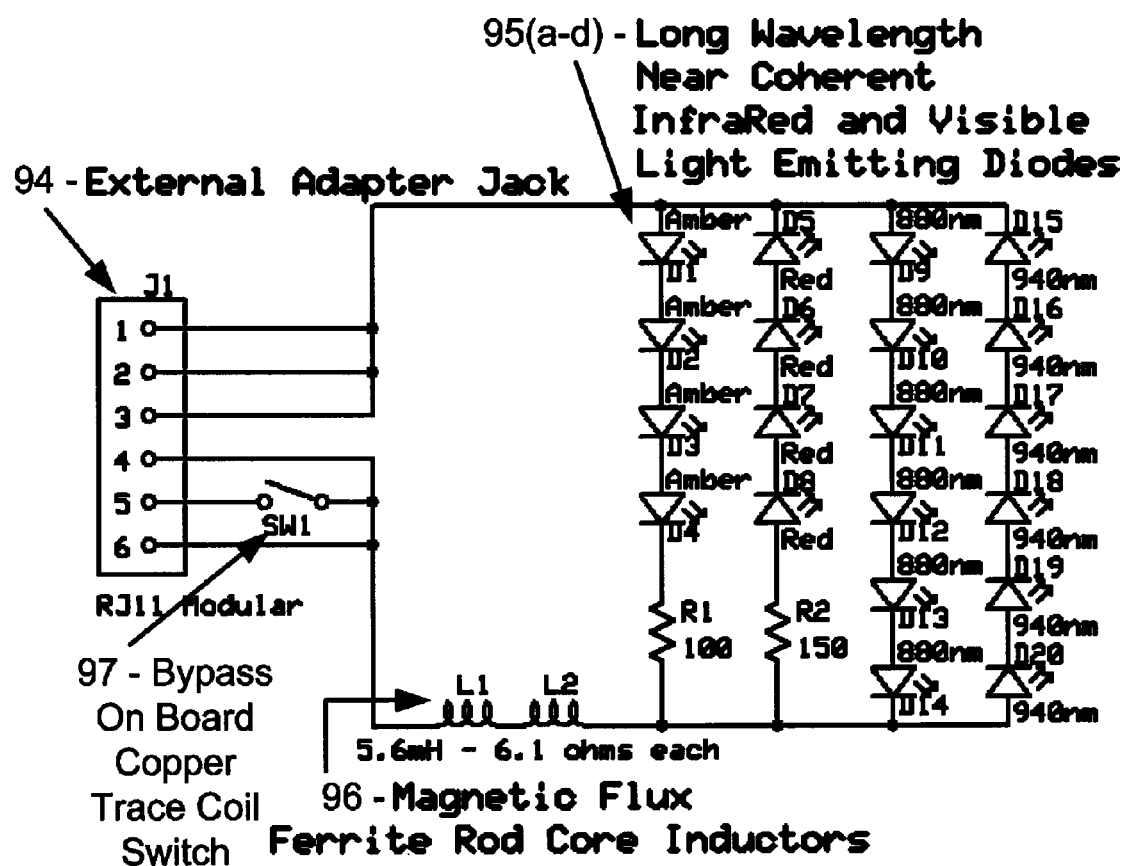
FIG. 15 is a schematic diagram of an external attachment to the EnergyWave Therapy Device that is used for spot treatments with both magnetic flux and light energies.
Figure 22:
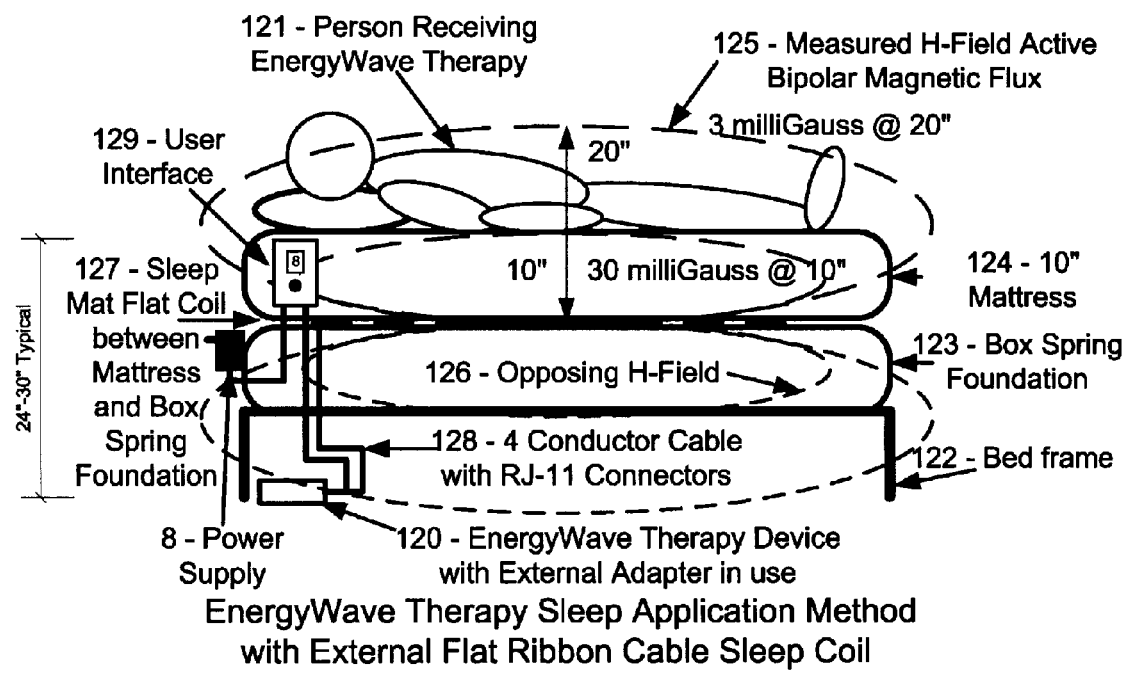
FIG. 22 is a drawing depicting a typical method of applying the device with an external sleep mat flat ribbon cable coil for a person sleeping.

First is the Sleep Mat Flat Coil 127 as depicted in FIGS. 14 and 22. This is constructed from 16 and-a-half feet of common 40 conductor flat ribbon cable 91 composed of 28 gauge copper stranded wire conductors. The female connector is crimped at one end of the cable as usual. At the other end of the cable, where the male header 92 will be crimped, the user first strips back the outer red striped wire (referred to as wire one) from the side of the cable about four inches back and then cuts the cable back to within half an inch of where the wire was stripped back. The newly cut main section of this end of the cable is placed in the male header 92 with wire number two, the new outside wire since number one with the red stripe was pulled back, in the number one position of the header. Another wire is pulled from the section that was just cut off and laid in the header next to wire number 40 that is now an open space in the header. The header backing is put in place and the cable is crimped as usual with the original red striped wire number one pulled free, uncrimped from the header 92 and the new wire number forty that was added to the header being the two ends of the 40 turn air core cable. These two ends are soldered to longer wires, typically 6 feet in length, which is then crimped into the center two pins of a modular RJ-11 or RJ-25 plug 93. The ribbon cable is folded to form a rectangular shape approximately 5 feet in length by 3 feet wide for a single or double bed. Alternatively, it may be folded to be 4 feet on each side for a queen or king sized bed application. Folded Sleep Mat Flat Coil 127 is then placed between the mattress 124 and box spring foundation 123 as shown in FIG. 22. If mattress 124 is less than 10 inches in depth, then Sleep Mat Flat Coil 127 should be placed under Box Springs Foundation 123, and may be placed on the floor under the bed, as long as the total distance between Sleep Mat Flat Coil 127 and the Person 121 is no more than 28 inches. Input plug 93 is then connected into Adapter Jack 12 of either embodiment of EnergyWave Therapy Device 120. Sleep Mat Flat Coil 127 is the preferred adapter when Person 121 is sleeping on a mechanical bed that has a metal understructure that can adversely disperse the magnetic flux field.

Figure 16:
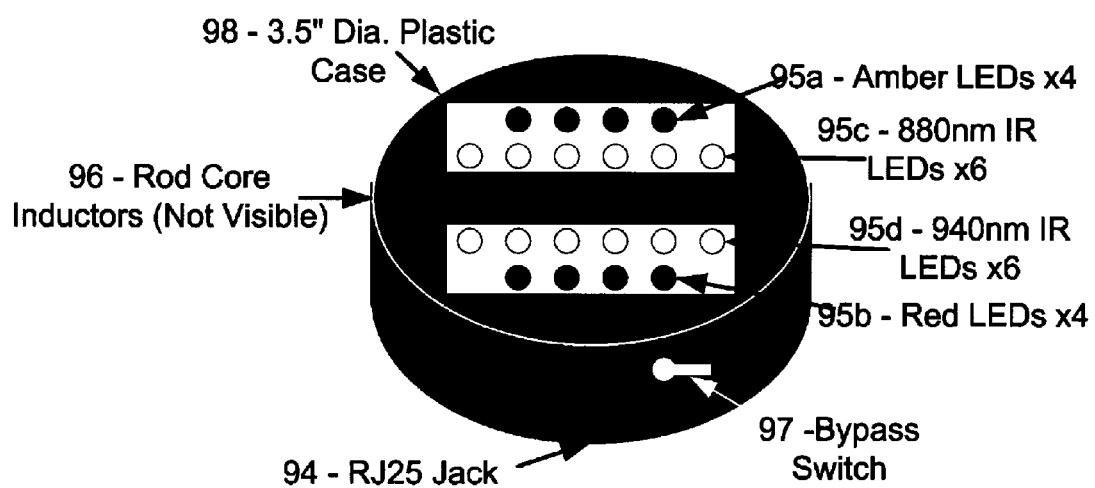
FIG. 16 is an assembled version of the attachment depicted in FIG. 15.
Figure 21:
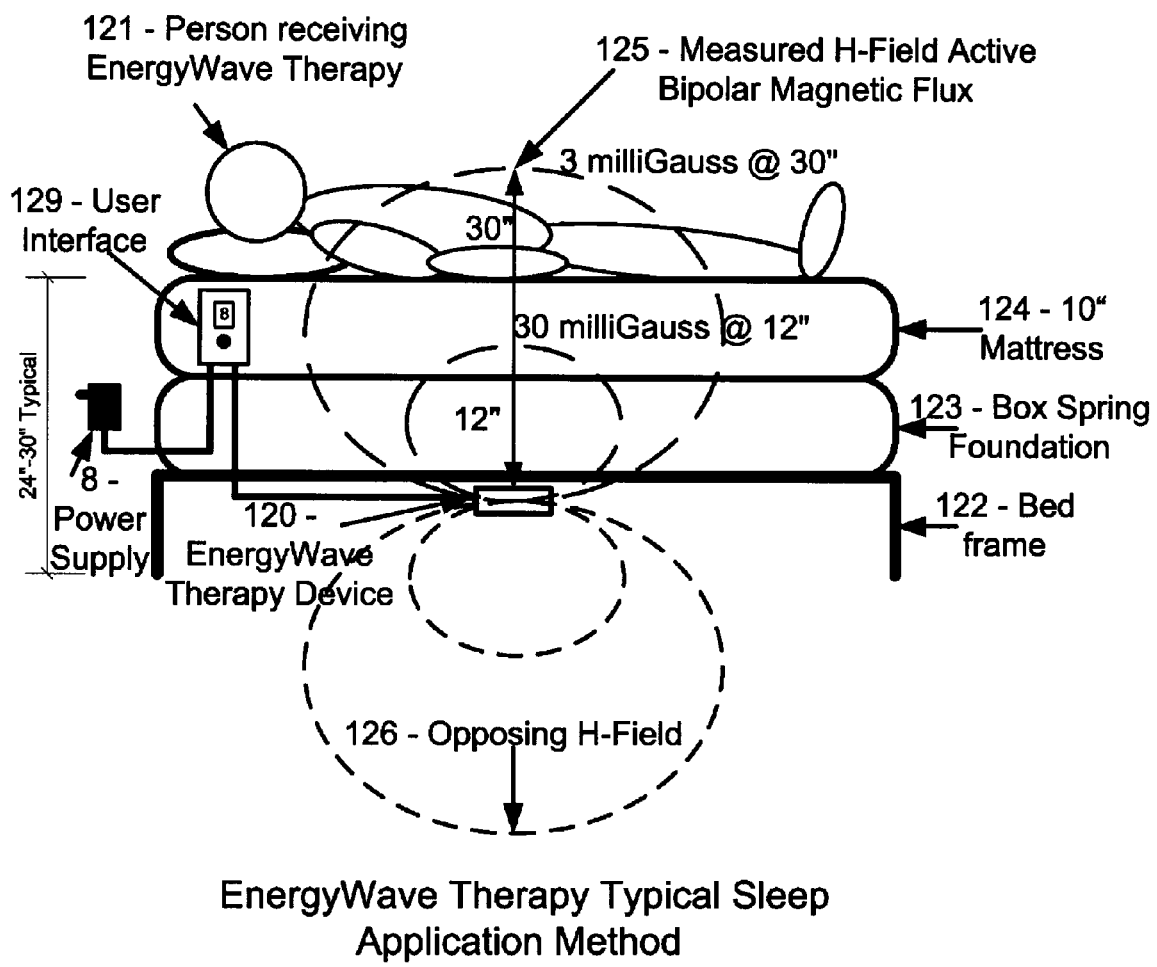
FIG. 21 is a drawing depicting a typical method of applying the device for a person sleeping.
Figure 27:
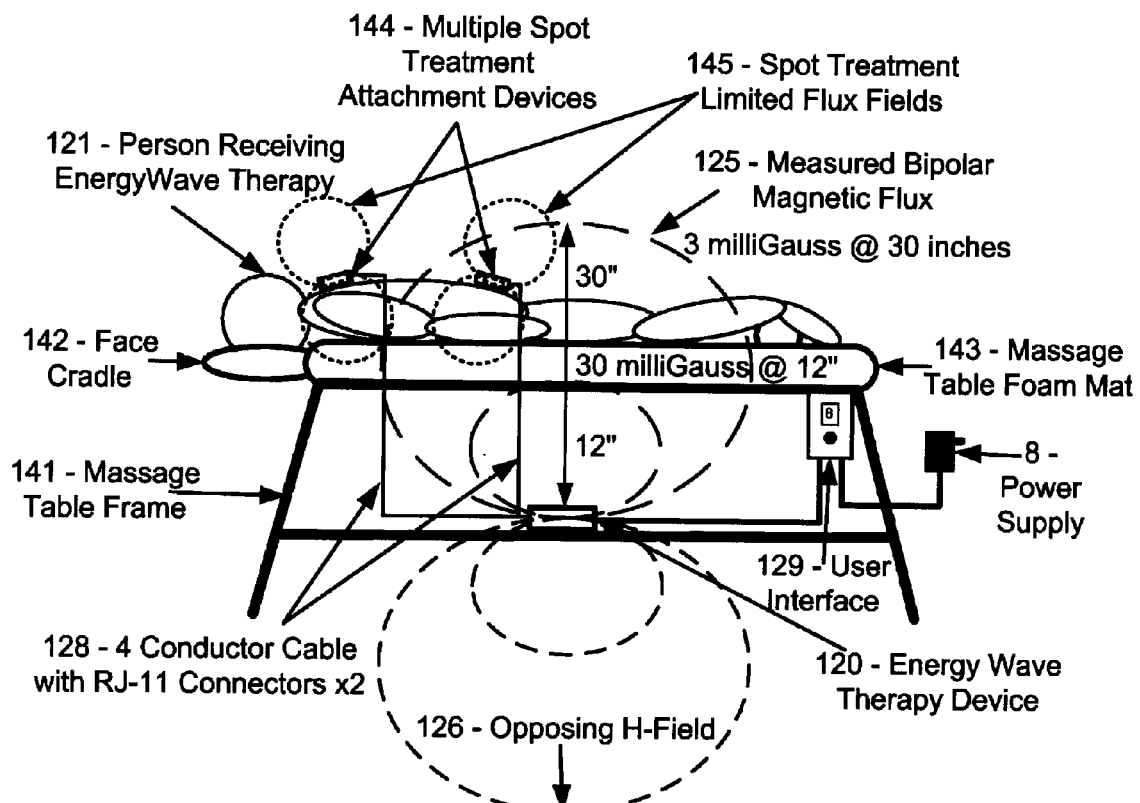
FIG. 27 is a drawing depicting a typical method of applying the device with external spot treatment attachments during massage therapy.

The second external EnergyWave adapter is the Spot Treatment Multiple Energies Attachment 144 (Spot Treatment Attachment) shown schematically in FIG. 21 with its assembled drawing in FIG. 16, and its application method in FIGS. 27. Spot Treatment Attachment 144 is constructed with two 5.6 milliHenry Rod Core Inductors 96 with a DC resistance of 6.1 ohms each connected in series with four strands of Light Emitting Diodes (LEDs) 95 $a$ through $d$. The LEDs are wired in series by wavelength, anode to cathode, with the four Amber 95$a$ LEDs' anode end connected through a 100 ohm R1 resistor to the Rod Core Inductors 96. The four Red 95$b$ LEDs cathode end is connected through a 150 ohm series resistor to the Rod Core Inductors 96. The six 880 nm Infrared 95$c$ LEDs anode end is connected to the Rod Core Inductors 96. The six 940 nm Infrared 95$d$ LEDs cathode end is connected to the Rod Core Inductors 96. This allows the four Amber 95$a$ LEDs to be illuminated at the same time as the six 880 nm Infrared 95$c$ LEDs, and the four Red 95b LEDs to be illuminated at the same time as the six 940 nm Infrared 95$d$ LEDs when the current flow is reversed by H-Bridge 7. The components are attached through its own Printed Circuit Board and then placed within a 3 and-one-half inch clear plastic case 98 shown in FIG. 16 with cutouts for External AdapterJack 94 and Bypass Switch 97. Bypass Switch 97 allows On Board Copper Trace Coil 10 in EnergyWave Therapy Device 120 to be turned on or off, thereby allowing Person 121 to selectively have Spot Treatment Attachment 144 used with or without the whole body Magnetic Flux 125. Spot Treatment Attachment 144 has a one hundred percent duty cycle since the reversing current will change the polarity of the magnetic flux emitted by Rod Core Inductors 96 and two of the series of LEDs 95 will be illuminated such that visible and Infrared energies of different wavelengths are constantly striking the Person 121 as illustrated in FIG. 27. More usage information is covered in the Applications and Methods section.

Figure 17:
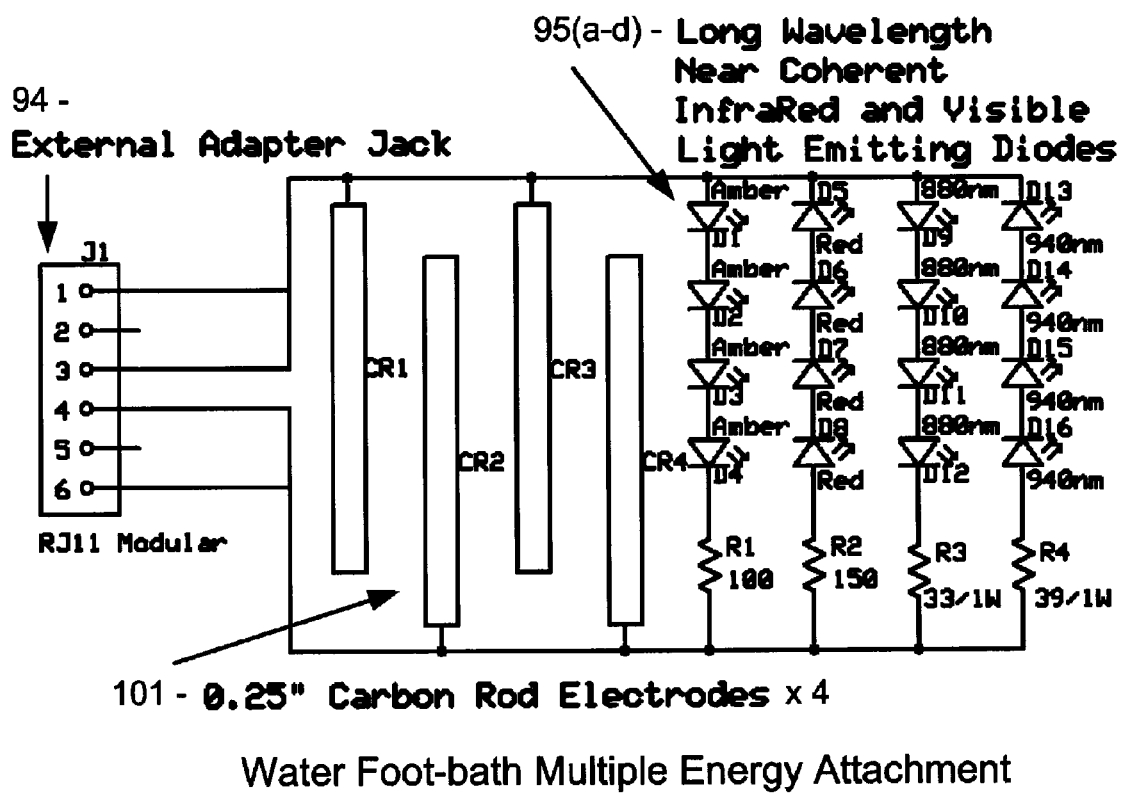
FIG. 17 is a schematic diagram of an external attachment to the Energy Wave Therapy Device used for the water foot-bath application.
Figure 18:
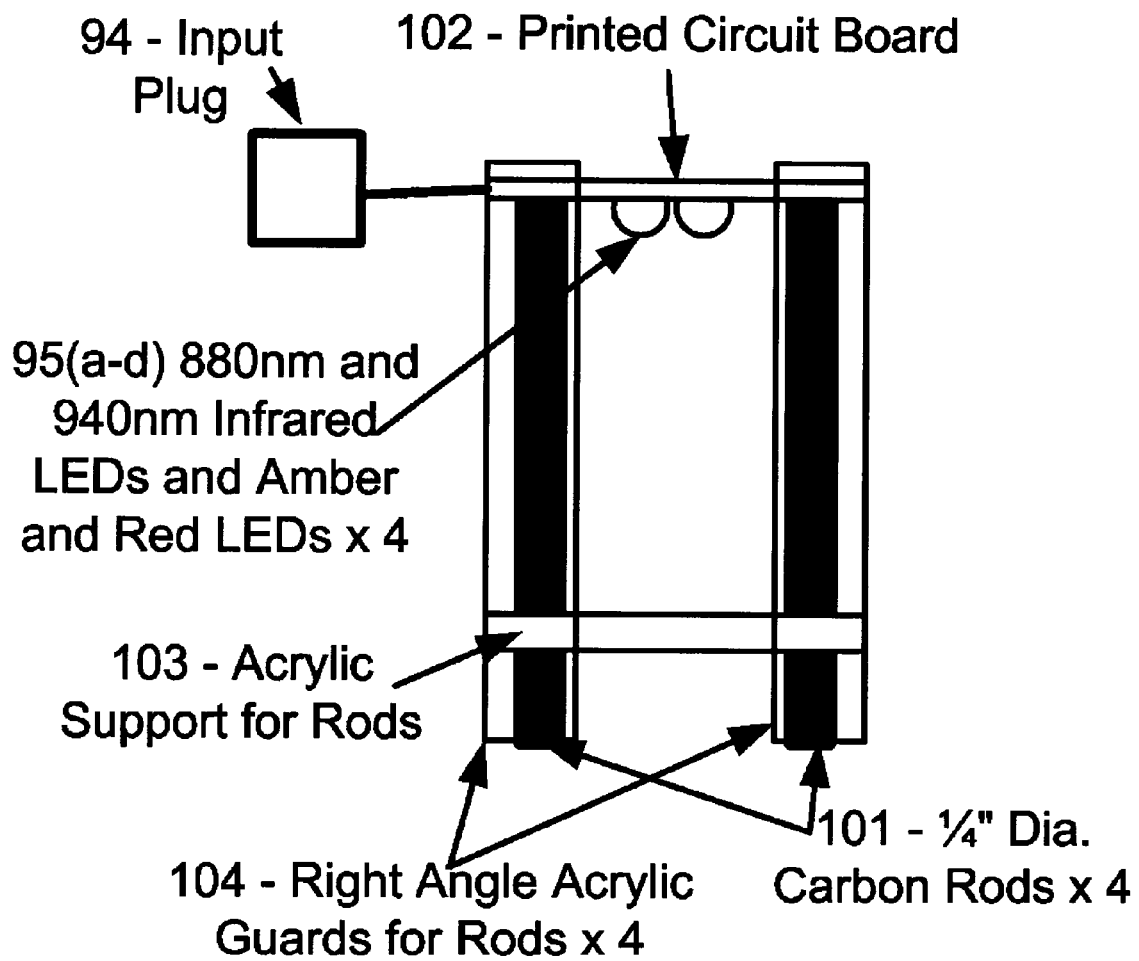
FIG. 18 is an assembled version of the attachment depicted in FIG. 17.
Figure 24:
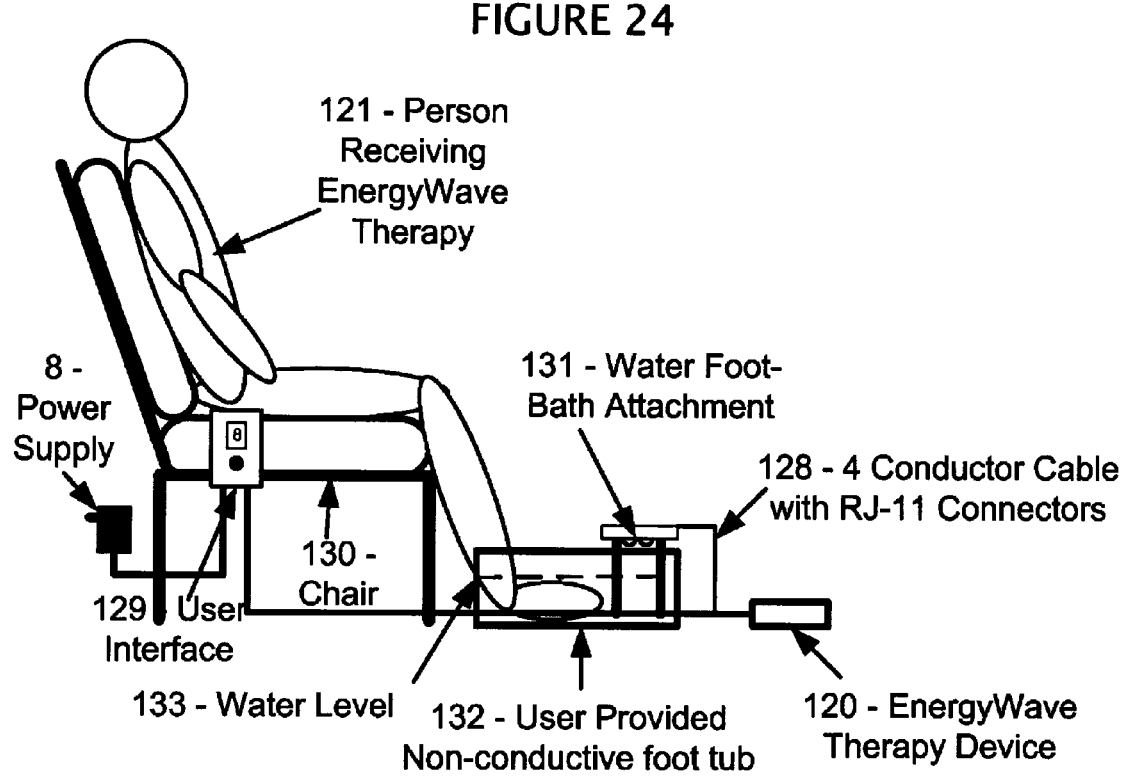
FIG. 24 is a drawing depicting a typical method of applying the device with the external foot-bath attachment in a water based foot-bath.

The third external EnergyWave adapter is the Water Foot-Bath Attachment 131 as shown in application FIG. 24, with its schematic shown in FIG. 17 and assembly in FIG. 18. This attachment is designed to be used in a water foot-bath application where Person 121 has his or her bare feet placed in water with the Water Foot-Bath Attachment 131 in the same water, but not in contact with Person 121's feet. Attachment 131 as depicted in FIGS. 17 and 18 is constructed with a Printed Circuit Board 102 that hosts the same type LEDs 95$a$-$d$ as used in Attachment 144 and four quarter inch diameter common non-coated gouging carbon rods 101 six inches in length. Carbon rods 101 are connected to Attachment 131's PCB through either quarter inch internal diameter opening metal push nuts which are soldered to the PCB, or through standard quarter inch metal fuse ends soldered to the PCB. Attachment 131 as depicted in FIGS. 17 and 18 attaches to controller 120 using jack 94. Four seven inch long acrylic right angle corners 104 are attached to each corner of the PCB as illustrated in FIG. 18 and to the acrylic support 103 for Carbon Rods 101. Acrylic Support 103 is the same external dimensions as the PCB for Attachment 131 and has four holes drilled into it to match the placement of Carbon Rods 101 to allow carbon rods 101 to pass through acrylic support 103. Modular Input Plug 94 is attached via six to ten feet of two conductor wire to the PCB for Attachment 131. Water Foot-Bath Attachment 131 has a one hundred percent duty cycle since the reversing current will change the current flow between the pairs of Carbon Rods 101 and two of the series of LEDs 95$a$-$d$ will be illuminated such that visible and Infrared energies of different wavelengths are constantly striking the Person 121 as illustrated in FIG. 24. More usage information is covered in the Applications and Methods section.

Applications and Methods

FIG. 21 through 27 inclusive illustrate some of the possible applications and methods of using various embodiments of the EnergyWave Therapy Device apparatus. These are discussed in detail in this section. The methods below assume the preferred embodiment of the apparatus, referred to as EnergyWave Therapy Device 120 or simply Device 120 is being used in conjunction with User Interface 1 as shown in FIGS. 12 and 13, and referred to as item 129 in the Applications and Methods FIGS. 21 to 27.

FIG. 21 illustrates the most commonly used method of applying the Alternating Polarity Magnetic Flux 125 to Person 121 while sleeping, napping or resting while lying on a suitable surface. Testing has demonstrated that a typical inner coil spring Mattress 124 and Box Spring Foundation 123 supported by bed frame 122 act to evenly disperse Flux 125 to provide a wide area of coverage for Person 121. The Opposing H-Field 126 is an equal, but opposite electromagnetic field that may be used for measurements and provides no known therapeutic effect to person 121. EnergyWave Therapy Device 120 should be placed at least 8 inches, but no more than 28 inches, from Person 121. The software loaded in Device 120 is designed to automatically start when power is applied, such that Person 121 need only press Switch 63 on User Interface 129 to start the preset program if Power Supply 8 is already plugged unto an appropriate AC outlet, or plug in Power Supply 8 into an appropriate AC outlet and the software will load the last run preset program and begin executing it after the five second delay to allow the user to change to a different preset program, if desired. All of the preset sleep programs begin at a frequency that is prevalent in a waking state and then begin stepping to lower frequencies during the first sleep cycle and thereafter follow the natural Circadian rhythms for an eight hour sleep cycle. All of the preset sleep programs include an energizing cycle at the end of seven hours of sleep, such that during the last hour the frequency increases to naturally awaken Person 121. At the end of the sleep cycle the preset program finishes, the software displays the numeral zero to indicate the program has completed and Device 120 stops emitting any further APMF signals. Person 121 can leave Power Supply 8 plugged into the appropriate AC outlet continuously and simply press Switch 63 on User Interface 129 to begin the same preset sleep program again the next time.

If Person 121 wanted to take a nap and Device 120 was configured with a shortened sleep program suitable for napping, then Person 121 would press Switch 63 once on User Interface 129 and the display would show the number of the preset program to be run and Person 121 would press Switch 63 repeatedly to step to the desired preset program number. After five seconds the newly selected program would begin running. When the preset program completed User Interface 129 displays the numeral zero to indicate such. When Person 121 returned to sleep for the night, Person 121 would press Switch 63 to start the process and then repeatedly press Switch 63 to step to the desired preset sleep program, as Device 120 uses Data EEPROM to save the last program run to support auto-start when powering up.

An alternative is shown in FIG. 22. In this method Sleep Mat Flat Coil 127 is connected to Adapter Jack 12 on Device 120 to be used as the emitter for the APMF energy waves through four conductor cable 128. This is desirable for mechanical beds or beds where it is impractical to place Device 120 within the 18 inch limitation of distance between Person 121 and Device 120. User Interface 129 may then be placed within convenient reach of person 121. In this method Sleep Mat 127 is inserted between the Mattress 124 and Box Springs Foundation 123 supported by bed frame 122, if Mattress 124 is at least ten inches in thickness. For thinner mattresses, Sleep Mat 127 should be placed under Box Springs Foundation 123, but within the 28 inch distance limitation. Opposing H-Field 126 offers no known therapeutic benefits but may be used for making flux measurements as it operates equally in the opposing direction. The operation of Device 120 through User Interface 129 for Person 121 is the same in this method as in FIG. 21.

Figure 23:
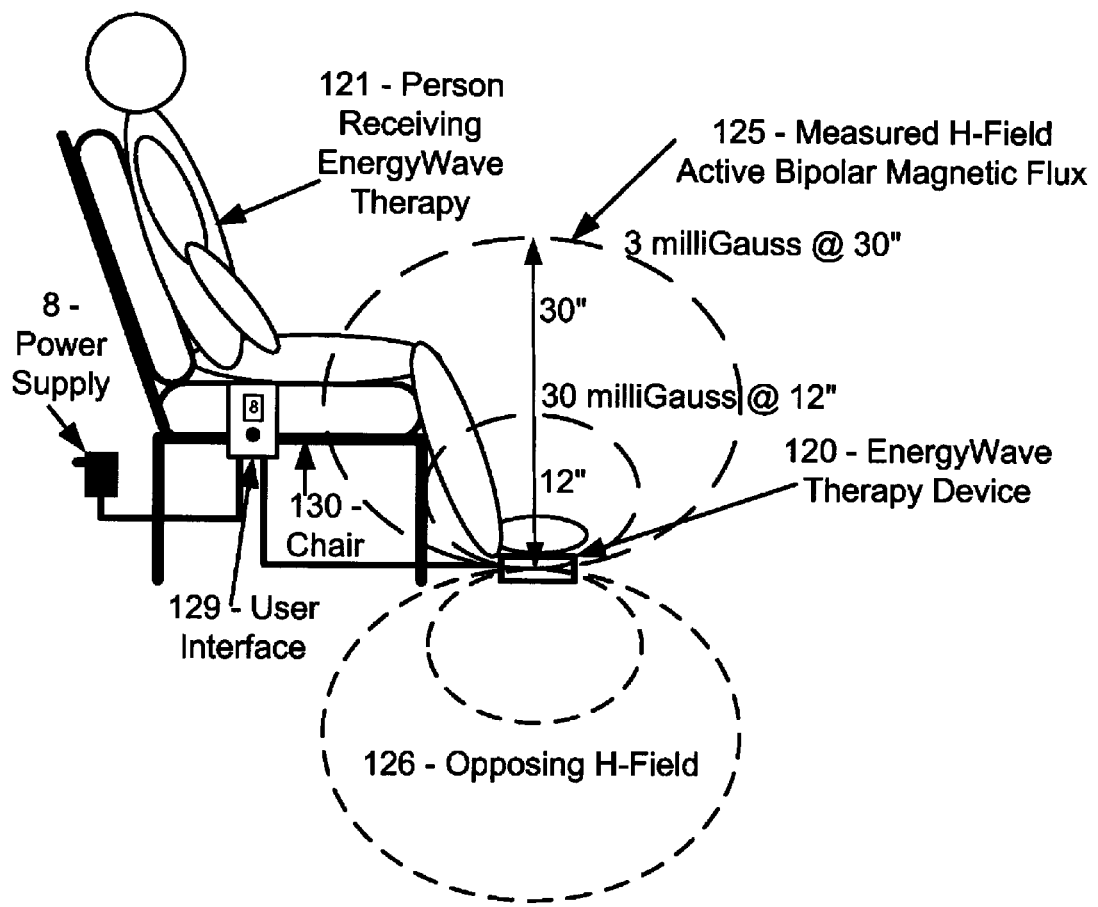
FIG. 23 is a drawing depicting a typical method of applying the device as a waterless foot-bath.

There are two foot-bath methods for using Device 120. The first is depicted in FIG. 23, and is referred to as the Waterless Foot-Bath. In this method of use, Person 121 may sit in a chair, or recline as desired, and Device 120 is placed in close proximity to Person 121's feet. There is a specific preset therapeutic program designed for the foot-bath method. When Device 120 is powered on, Person 121 presses Switch 63 on User Interface 129 during the five second delay to select the foot-bath preset program. The program runs thirty minutes and auto-shuts off with User Interface 129 displaying the numeral zero to indicate the program is completed.

The second foot-bath method is shown in FIG. 24 and requires the use of the Water Foot-Bath Attachment 131 to be connected via Cable 128 to Device 120. Person 121 must supply a suitable foot tub sufficient in size to accommodate Person 121's feet and Attachment 131 and hold about one gallon of water. The water level should cover Person 121's feet, but not be so high as to come in contact with the connector or PCB assembly portion of Attachment 131. Person 121 operates the foot-bath in the same manner through User Interface 129 as described in the waterless foot-bath method. At the conclusion of the water foot-bath treatment, which runs for 30 minutes, Person 121 removes his or her feet from the foot tub and dries them completely before touching Device 120 or anything connected to it, especially Power Supply 8.

Figure 25:
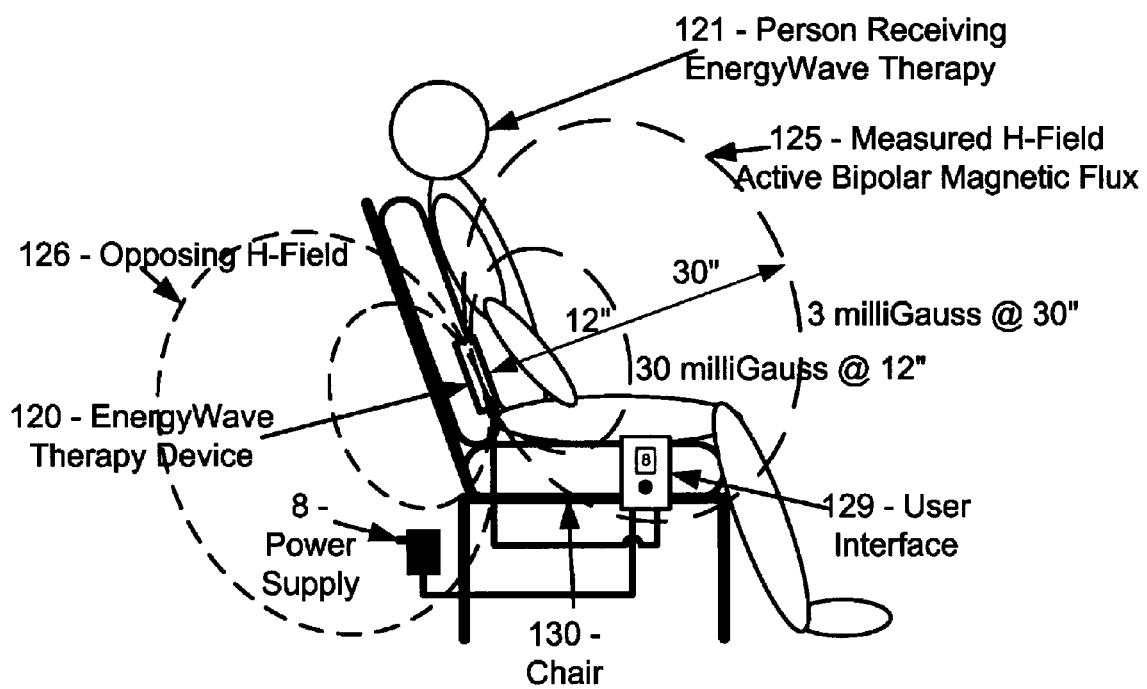
FIG. 25 is a drawing depicting a typical method of applying the device for spot treatment to a specific part of the body, in this example the lumbar region of the person's back.

For treating sore muscles or joints Device 120 may be placed in direct contact with the sore or injured area for local treatment as depicted in FIG. 25. Again, the Foot Bath preset program is used in this method. Device 120 is powered on and placed next to the area to be treated by placing either the top cover or bottom cover of the device as close as possible to the affected area. Person 121 again follows the User Interface procedures as described in the waterless foot-bath method of operation. Device 120 will get slightly warm during use at it will generate, and hence need to dissipate, two to four watts of heat energy.

Figure 26:
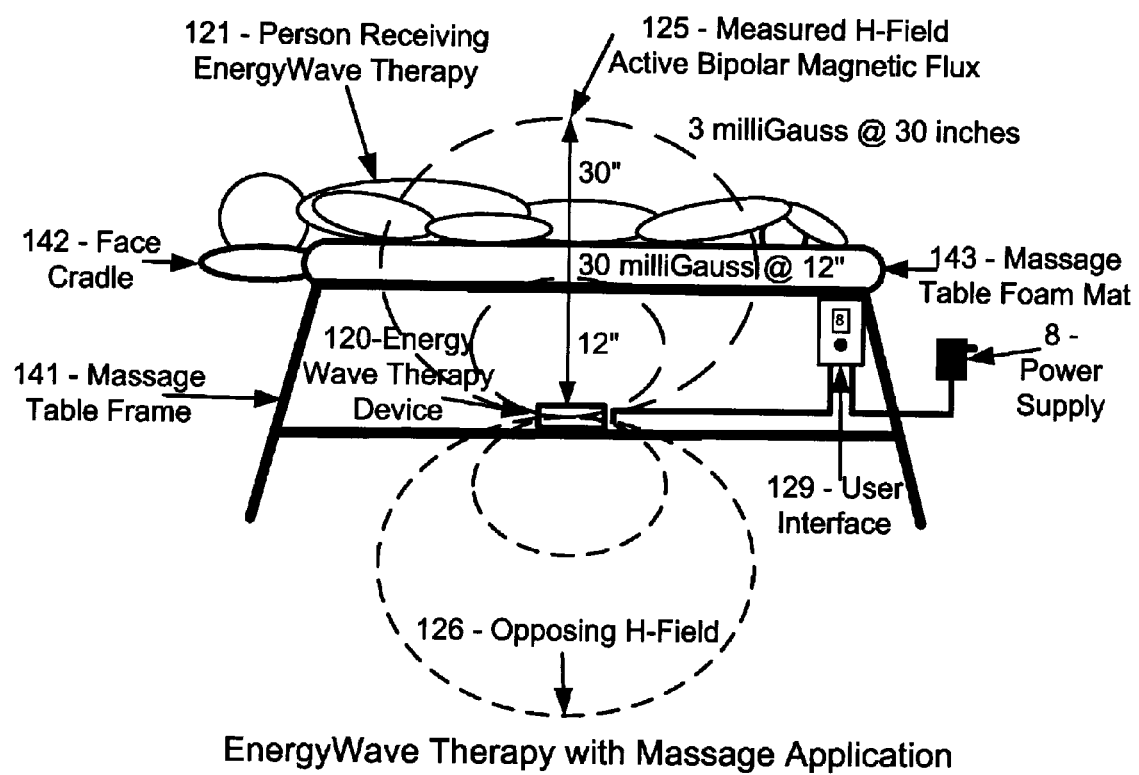
FIG. 26 is a drawing depicting a typical method of applying the device for use during massage therapy.

EnergyWave Therapy Device 120 has been tested and used extensively in therapeutic massage applications, and FIGS. 26 and 27 illustrate two methods of use. In the typical therapeutic massage method, Device 120 is placed on the supporting framework or utility table under the foam mat which supports Person 121. Device 120 should be located within twelve inches of Person 121, but not closer than four inches. While any of the sleep programs could be used in this method, there exists special therapeutic programs developed specifically for this method of operation that may be selected by a trained massage practitioner familiar with EnergyWave Therapy Device 120 for a particular setting. A separate Utility Patent is being prepared to cover the various methods of delivering massage in conjunction with the use of Device 120 or similar devices; hence this section only deals with the specifics of Device 120's operation. In this method of operation both the massage practitioner and Person 121 benefit from the healing environment of Device 120.

FIG. 27 depicts the method for use with the External Spot Treatment Attachments 144 used in conjunction with Device 120. H-Bridge 7 and Power Supply 8 are sized to handle up to one and one-half amperes of current, and this configuration uses only half that much current. In this method, Person 121 receives the overall treatment field from Device 120 and also spot treatments from Attachments 144. Attachments 144 are placed according to the need to treat specific locations that are particularly inflamed, sore, or otherwise in pain and discomfort. Testing to date has shown remarkable improvements for stiff joints, sore muscles and even relief from TMJ symptoms when used in conjunction with a qualified massage practitioner, physical therapist or chiropractor.

Alternative Embodiments

Figure 19:
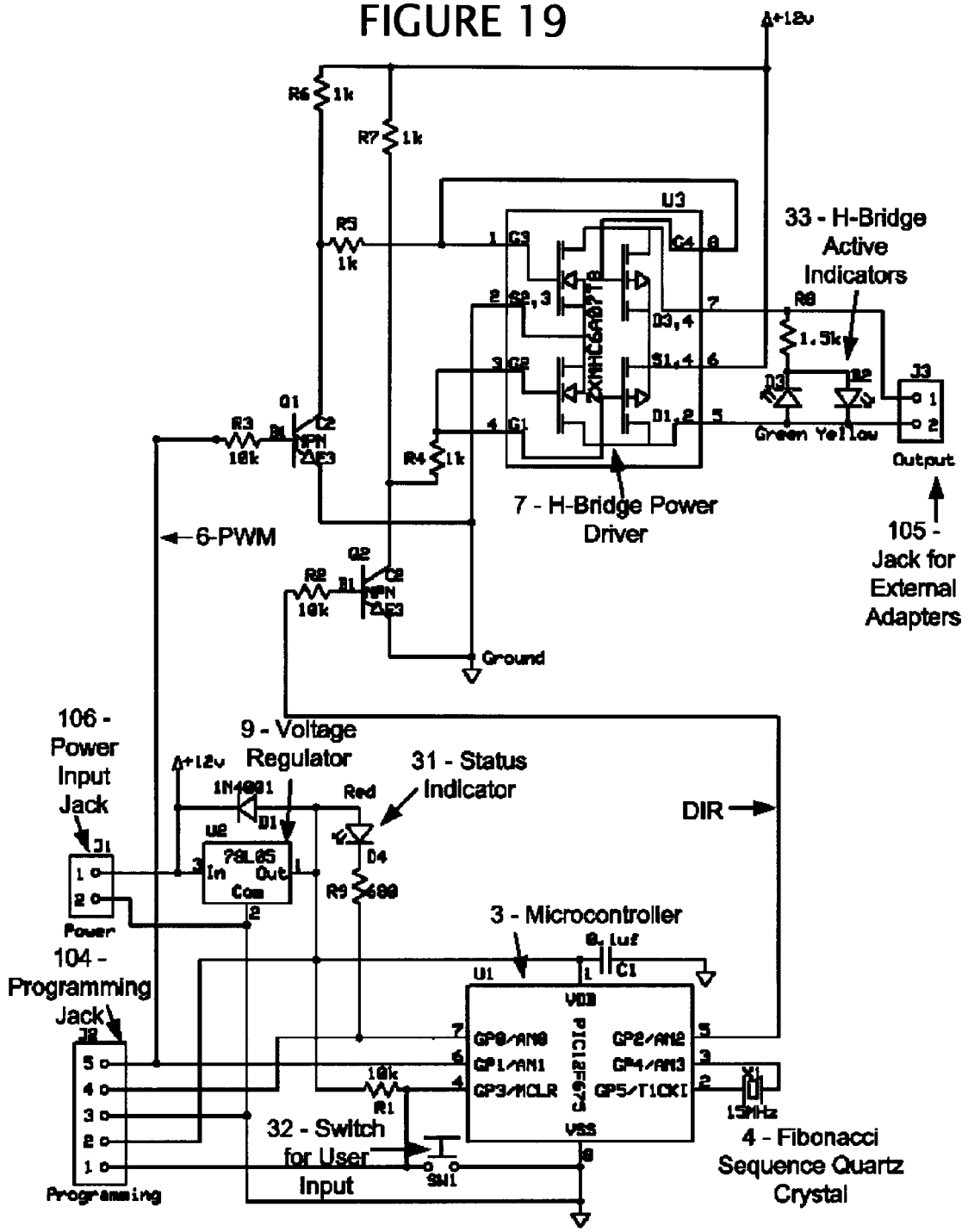
FIG. 19 is a schematic diagram for one alternative lower cost embodiment of the EnergyWave Therapy Device PCB.
Figure 20:
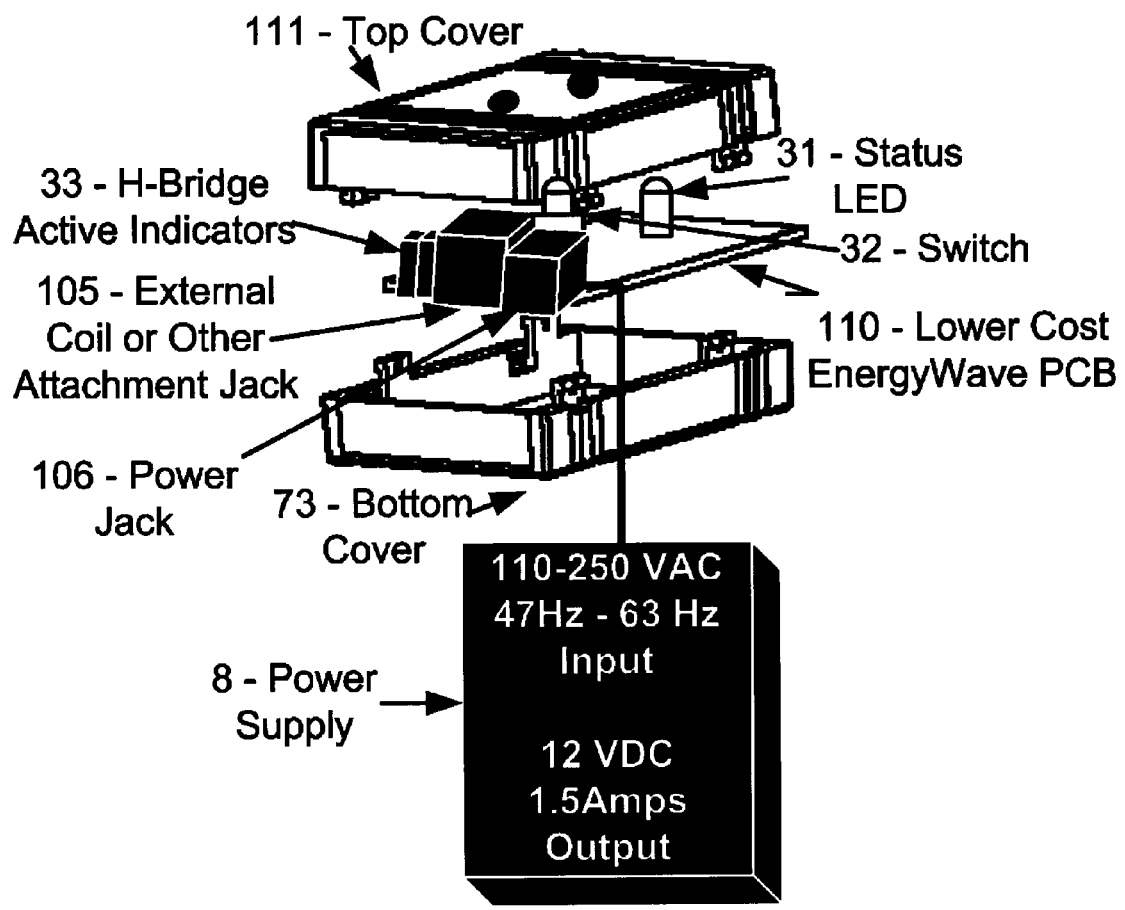
FIG. 20 is an assembly drawing for the alternative PCB depicted in FIG. 19.

FIGS. 19 and 20 depict an alternative embodiment using a lower cost H-Bridge 7 and lower cost assembly and requiring the use of an external energy wave emitter. This alternative embodiment is shown to illustrate an even lower cost option for delivering energy wave therapy, or to support self contained spot treatment devices assembling the PCB in FIG. 19 inside the Spot Treatment Attachment 144 assembly shown in FIG. 16.

A second alternative embodiment that has been produced and tested uses the optional components in the schematic of the preferred embodiment in FIG. 8, being Status Indicator 31, Switch 32 and H-Bridge Active Indicators 33 with no external User Interface 1. In this embodiment Power Supply 8 connects directly to Device 120 through Connector 2 and Device 120 is controlled via the on-board Status Indicator 31 and Switch 32. This is well suited for applications where the same preset program is used repeatedly and Person 121 does not need to change it on a regular basis. In this method of operation an inline power cord switch, not shown, is installed in the power line between Power Supply 8 and Connector 2 to allow Person 121 to turn Device 120 on which will then auto-start after the five second delay and then turn Device 120 off at the end of the preset program cycle. Alternatively, a timed AC circuit switch, similar to those used to turn lamps on and off at preset times, may be used to start Device 120 at the same time each night and turn it off in the morning.

Figure 28:
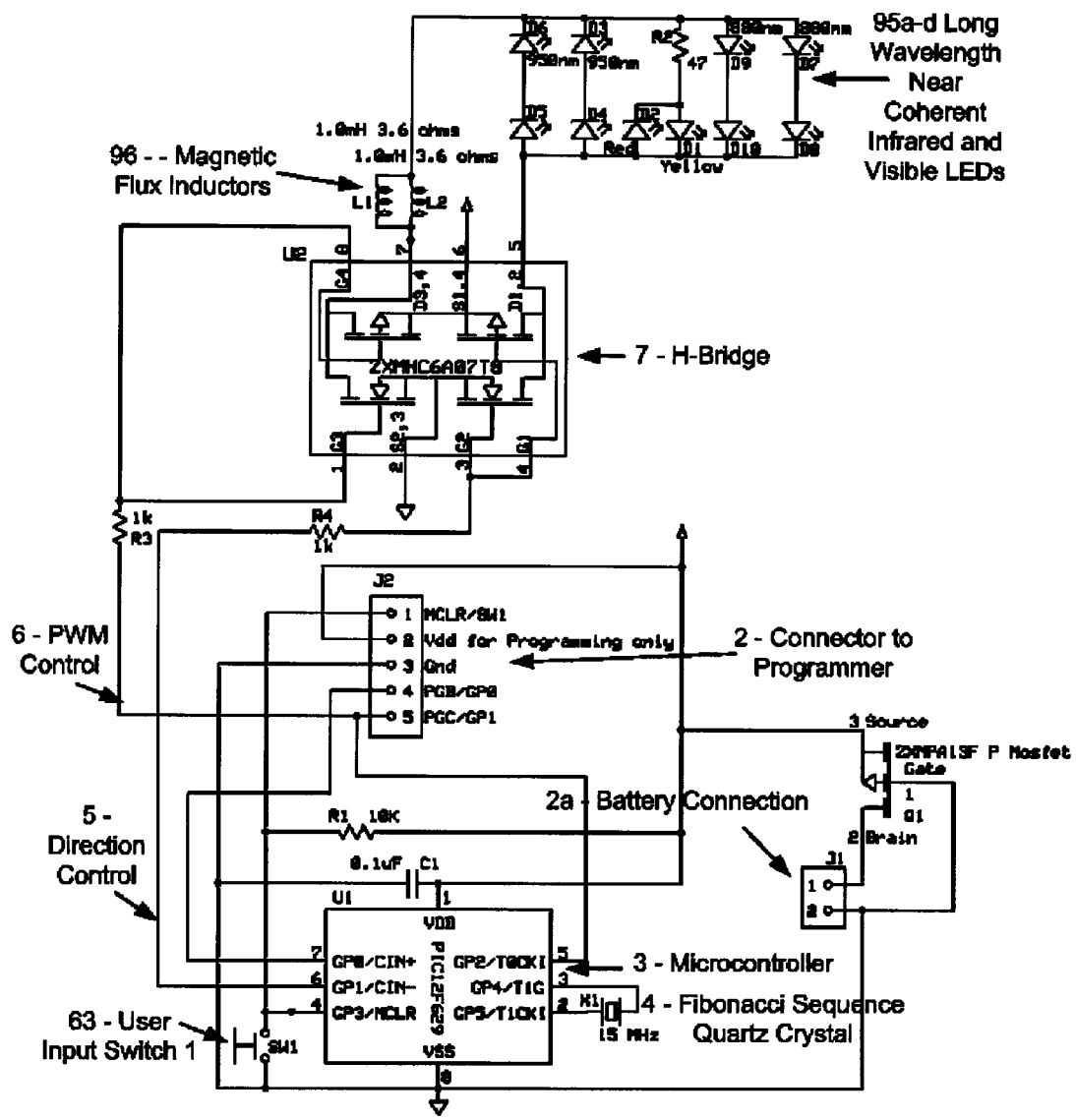
FIG. 28 is a schematic of the battery powered Integrated EnergyWave Therapy Device alternative embodiment.

A third alternative embodiment is shown schematically in FIG. 28 and is referred to as an Integrated EnergyWave Therapy Device which incorporates the spot treatment capabilities and the User Interface functions in a battery powered version.

Another alternative is using the smaller format of the sleep mat in a chair or automobile car seat. In the automotive application the apparatus can be powered by the 12 VDC power outlets available in mobile applications.

There are other alternative embodiments of this invention that one familiar in the art could conceive and these should be considered as being covered by this art.

The embodiments of the EnergyWave Therapy Device overcome the existing disadvantages of current electromagnetic therapy devices by its novel use of several common components that have been brought together for the first time in this unique apparatus. While numerous patents have been granted for electromagnetic therapy devices, this invention presents a new approach with significant improvements creating an EnergyWave Therapy Device that has been proven to be effective in improving sleep, reducing pain and encouraging natural healing, and lower in cost to produce while being safer and simpler to use.

| Definition List 1 | |
|---|---|
| Term | Definition |
| APMF | Alternating Polarity Magnetic Fields |
| AC | Alternating Current |
| CMOS | Complementary Metal Oxide Substrate |
| cps | Cycles Per Second |
| CRT-Ps | Cardiac Resynchronization Therapy Pacemakers |
| DC | Direct Current |
| DMOS | Double-diffused Metal Oxide Substrate |
| E | Electromotive Force measured in Volts |
| ELF | Extremely Low Frequencies (below 10,000 Hz) |
| EMF | Electro Magnetic Field |
| EMI | Electro Magnetic Interference |
| G | Gauss, measurement, magnetic strength |
| H | H Field, magnetic field |
| Hz | Hertz, cycles per second |
| I/O | Input/Output data lines |
| IC | Integrated Circuit |
| ICD | Implantable Cardioverter Defibrillator |
| LED | Light Emitting Diode |
| mG | milliGauss, weak magnetic measurement |
| mT | milliTeslas, equal to 10 Gauss |
| MSELF | Multiple Simultaneous Extremely Low Frequency |
| PCB | Printed Circuit Board |
| PWM | Pulse Width Modulation |
| REM | Rapid Eye Movement, associated with dreaming |
| T | Tesla, a measure of very strong magnetic fields |
| uT | microTeslas, a measure of weak magnetic fields equal to 10 milliGauss |

What is claimed is:

1. An apparatus comprising:
a Fibonacci number quartz crystal, wherein the Fibonacci number quartz crystal has a fundamental frequency with a deviation of less than 0.5% from a Fibonacci number;
a processor;
an electromagnetic emitter;
a storage device storing a waking circadian pattern, wherein the waking circadian pattern comprises a sequence of electromagnetic pulses corresponding to waking levels of brainwave activity in an organism; and
the storage device further storing instructions for controlling the processor to perform steps comprising:
producing a first signal having a first frequency based at least in part on the fundamental frequency of the Fibonacci number quartz crystal and the waking circadian pattern;
producing a second signal having a second frequency based at least in part on the fundamental frequency of the Fibonacci number quartz crystal and the waking circadian pattern, wherein the second frequency is greater than the first frequency;
producing a mixed bi-polar signal by mixing the first signal and the second signal through an H-bridge; and
emitting the mixed bi-polar signal via the electromagnetic emitter, to yield an emitted mixed bi-polar signal.

2. The apparatus of claim 1, wherein the electromagnetic emitter comprises a least one of a light-emitting diode and a metallic coil.

3. The apparatus of claim 2, wherein the wavelength of the light emitting diode is in the inclusive range of visible and infrared light.

4. The apparatus of claim 1, wherein the Fibonacci number quartz crystal further comprises a fundamental frequency greater than 1,000,000 Hz.

5. The apparatus of claim 1, further comprising a user interface.

6. The apparatus of claim 5, wherein the storage device having additional instructions stored which result in the steps further comprising:
receiving, via the user interface, a user input; and
modifying at least one of an intensity of the emitted mixed bi-polar signal, the first frequency, the second frequency, and a time length for operation of the apparatus based on the user input.

7. An apparatus comprising:
a Fibonacci number quartz crystal, wherein the Fibonacci number quartz crystal has a fundamental frequency with a deviation of less than 0.5% from a Fibonacci number;
a processor;
a plurality of electromagnetic emitters;
a storage device storing a waking circadian pattern, wherein the waking circadian pattern comprises a sequence of electromagnetic pulses corresponding to waking levels of brainwave activity in an organism; and
the storage device further storing instructions for controlling the processor to perform steps comprising:
producing a first signal having a first frequency based at least in part on the fundamental frequency of the Fibonacci number quartz crystal and the waking circadian pattern;
producing a second signal having a second frequency based at least in part on the fundamental frequency of the Fibonacci number quartz crystal and the waking circadian pattern, wherein the second frequency is greater than the first frequency;
producing a mixed bi-polar signal by mixing the first signal and the second signal through an H-bridge; and
emitting the mixed bi-polar signal via the plurality of electromagnetic emitters, to yield an emitted mixed bi-polar signal.

8. The apparatus of claim 7, wherein the plurality of electromagnetic emitters comprises at least one of a light-emitting diode and a metallic coil.

9. The apparatus of claim 8, wherein the wavelength of the light emitting diode is in the inclusive range of visible and infrared light.

10. The apparatus of claim 7, wherein the Fibonacci number quartz crystal further comprises a fundamental frequency greater than 1,000,000 Hz.

11. The apparatus of claim 7, further comprising a user interface.

12. The apparatus of claim 11, wherein the storage device has additional instructions stored which result in the steps further comprising:
- receiving, via the user interface, a user input; and
- modifying at least one of an intensity of the emitted mixed bi-polar signal, the first frequency, the second frequency, a time length for operation of the apparatus, and a sub-group of the plurality of electromagnetic emitters based on the user input.

13. An apparatus comprising:
- a Fibonacci number quartz crystal, wherein the Fibonacci number quartz crystal has a fundamental frequency with a deviation of less than 0.5% from a Fibonacci number;
- a processor;
- a plurality of electromagnetic emitters;
- a storage device storing a plurality of waking circadian patterns, wherein each waking circadian pattern within the plurality of waking circadian patterns comprises a sequence of electromagnetic pulses corresponding to waking levels of brainwave activity in an organism; and
- the storage device further storing instructions for controlling the processor to perform steps comprising:
  - selecting a unique waking circadian pattern from the plurality of waking circadian patterns;
  - producing a first signal having a first frequency based at least in part on the fundamental frequency of the Fibonacci number quartz crystal and the unique waking circadian pattern;
  - producing a second signal having a second frequency based at least in part on the fundamental frequency of the Fibonacci number quartz crystal and the unique waking circadian pattern, wherein the second frequency is greater than the first frequency;
  - producing a mixed bi-polar signal by mixing the first signal and the second signal through an H-bridge; and
  - emitting the mixed bi-polar signal via the plurality of electromagnetic emitters, to yield an emitted mixed bi-polar signal.

14. The apparatus of claim 13, wherein the plurality of electromagnetic emitters comprises at least one of a light-emitting diode and a metallic coil.

15. The apparatus of claim 14, wherein the wavelength of the light emitting diode is in the inclusive range of visible and infrared light.

16. The apparatus of claim 13, wherein the Fibonacci number quartz crystal further comprises a fundamental frequency greater than 1,000,000 Hz.

17. The apparatus of claim 13, further comprising a user interface.

18. The apparatus of claim 17, wherein the storage device having additional instructions stored which result in the steps further comprising:
- receiving, via the user interface, a user input; and
- modifying at least one of an intensity of the emitted mixed bi-polar signal, the first frequency, the second frequency, a time length for operation of the apparatus, a sub-group of the plurality of electromagnetic emitters, and the unique waking circadian pattern from the plurality of waking circadian patterns based on the user input.

19. The apparatus of claim 13, wherein each waking circadian pattern in the plurality of waking circadian patterns is configured to reflect an activity level of a user.

* * * * *